US010426958B2

(12) United States Patent
Loudin et al.

(10) Patent No.: US 10,426,958 B2
(45) Date of Patent: Oct. 1, 2019

(54) INTRANASAL STIMULATION FOR ENHANCED RELEASE OF OCULAR MUCINS AND OTHER TEAR PROTEINS

(71) Applicant: Oculeve, Inc., South San Francisco, CA (US)

(72) Inventors: James Donald Loudin, Houston, TX (US); Manfred Franke, Valencia, CA (US); Douglas Michael Ackermann, San Francisco, CA (US)

(73) Assignee: Oculeve, Inc., San Francisco, CA (US)

( * ) Notice: Subject to any disclaimer, the term of this patent is extended or adjusted under 35 U.S.C. 154(b) by 94 days.

(21) Appl. No.: 15/367,030

(22) Filed: Dec. 1, 2016

(65) Prior Publication Data

US 2017/0157401 A1 Jun. 8, 2017

Related U.S. Application Data

(60) Provisional application No. 62/263,498, filed on Dec. 4, 2015, provisional application No. 62/321,170, filed (Continued)

(51) Int. Cl.
*A61N 1/36* (2006.01)
*A61N 1/05* (2006.01)
(Continued)

(52) U.S. Cl.
CPC ........ *A61N 1/36046* (2013.01); *A61B 5/0488* (2013.01); *A61B 5/053* (2013.01);
(Continued)

(58) Field of Classification Search
CPC . A61N 1/36046; A61N 1/0546; A61B 5/6819
See application file for complete search history.

(56) References Cited

U.S. PATENT DOCUMENTS 2,512,882 A 6/1950 Truesdale
2,525,381 A 10/1950 Tower
(Continued)

FOREIGN PATENT DOCUMENTS

CN 1488331 A 4/2004
CN 101087822 A 12/2007
(Continued)

OTHER PUBLICATIONS

Acar, M. et al. (2013). "Ocular surface assessment in patients with obstructive sleep apnea-hypopnea syndrome," Sleep Breath 17(2):583-588.
(Continued)

*Primary Examiner* — George R Evanisko
(74) *Attorney, Agent, or Firm* — Mintz Levin Cohn Ferris Glovsky and Popeo, P.C.

(57) ABSTRACT

Described here are devices and methods for increasing ocular mucin and other tear protein release using intranasally delivered electrical stimulation. Generally, the devices may deliver electrical stimulation to the nasal mucosa. Intranasal stimulation may trigger degranulation of conjunctival goblet cells, which in turn releases secretory mucins into the tear fluid. The intranasal stimulation may also trigger release of lysozyme, lactoferrin, and other tear proteins into the aqueous layer of the tear film. The methods may further comprise obtaining feedback relating to the efficacy of the delivered electrical stimulation by measuring impedance or an electromyogram (EMG) signal.

36 Claims, 26 Drawing Sheets

Related U.S. Application Data on Apr. 11, 2016, provisional application No. 62/330,744, filed on May 2, 2016, provisional application No. 62/376,834, filed on Aug. 18, 2016.

(51) Int. Cl.
  *A61B 5/00* (2006.01)
  *A61B 5/0488* (2006.01)
  *A61B 5/053* (2006.01)

(52) U.S. Cl.
  CPC .......... *A61B 5/0538* (2013.01); *A61B 5/6819* (2013.01); *A61N 1/0546* (2013.01); *A61N 1/36014* (2013.01); *A61B 5/4848* (2013.01); *A61B 2562/04* (2013.01); *A61N 1/36031* (2017.08); *A61N 1/36034* (2017.08)

(56) References Cited

U.S. PATENT DOCUMENTS

| | | |
|---|---|---|
| 3,620,219 A | 11/1971 | Barker |
| 3,709,228 A | 1/1973 | Barker et al. |
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,935,155 A | 8/1999 | Humayun et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,389 B1 | 3/2008 | Newsome |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |

(56) References Cited

U.S. PATENT DOCUMENTS

| | | |
|---|---|---|
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 9,956,397 B2 | 5/2018 | Loudin et al. |
| D826,420 S | 8/2018 | Ackermann et al. |
| 10,143,846 B2 | 12/2018 | Ackermann et al. |
| D837,396 S | 1/2019 | Ackermann et al. |
| 10,207,108 B2 | 2/2019 | Franke et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0014089 A1 | 1/2003 | Chow et al. |
| 2003/0045909 A1 | 3/2003 | Gross et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0139784 A1 | 7/2003 | Morimoto et al. |
| 2003/0176898 A1* | 9/2003 | Gross ............... A61M 5/14276 607/54 |
| 2003/0192784 A1 | 10/2003 | Zhou et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0004625 A1 | 1/2005 | Chow |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0256570 A1 | 11/2005 | Azar |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0216317 A1 | 9/2006 | Reinhard et al. |
| 2006/0235430 A1 | 10/2006 | Le et al. |
| 2006/0239482 A1 | 10/2006 | Hatoum et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2006/0276738 A1 | 12/2006 | Becker |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299420 A1 | 12/2007 | Peyman |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109054 A1 | 5/2008 | Hastings et al. |
| 2008/0114424 A1 | 5/2008 | Grenon et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208335 A1 | 8/2008 | Blum et al. |
| 2008/0221642 A1 | 9/2008 | Humayun et al. |
| 2008/0269648 A1 | 10/2008 | Bock |
| 2008/0288036 A1 | 11/2008 | Greenberg et al. |
| 2008/0294066 A1 | 11/2008 | Hetling et al. |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |

(56) References Cited

U.S. PATENT DOCUMENTS

| | | |
|---|---|---|
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | DeMaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0077551 A1 | 3/2011 | Videbaek |
| 2011/0077698 A1 | 3/2011 | Tsampazis et al. |
| 2011/0082518 A1 | 4/2011 | Filippello |
| 2011/0093043 A1 | 4/2011 | Torgerson et al. |
| 2011/0151393 A1* | 6/2011 | Frey, II ................ A61B 17/24 433/24 |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0270067 A1 | 11/2011 | Faraji et al. |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1* | 12/2011 | De Vos ................ A61H 39/002 607/3 |
| 2012/0053648 A1 | 3/2012 | Neher et al. |
| 2012/0112903 A1 | 5/2012 | Kaib et al. |
| 2012/0130398 A1* | 5/2012 | Ackermann ........ A61N 1/36046 606/129 |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1* | 12/2012 | Wolf ................ A61B 18/1485 606/2 |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1 | 10/2013 | Otto et al. |
| 2013/0274831 A1 | 10/2013 | Otto et al. |
| 2013/0304154 A1 | 11/2013 | Goodman et al. |
| 2013/0310887 A1 | 11/2013 | Curtis |
| 2013/0336557 A1 | 12/2013 | Cruzat et al. |
| 2014/0012182 A1 | 1/2014 | Shantha et al. |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0163580 A1 | 6/2014 | Tischendorf et al. |
| 2014/0214120 A1 | 7/2014 | Simon et al. |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1* | 10/2014 | Ackermann ........ A61N 1/36046 601/46 |
| 2014/0316396 A1 | 10/2014 | Wolf et al. |
| 2014/0316485 A1 | 10/2014 | Ackermann et al. |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2015/0362755 A1 | 12/2015 | Lee et al. |
| 2016/0022992 A1 | 1/2016 | Franke et al. |
| 2016/0058615 A1 | 3/2016 | Camras et al. |
| 2016/0114163 A1 | 4/2016 | Franke et al. |
| 2016/0114172 A1 | 4/2016 | Loudin et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1* | 12/2016 | Kahook ............. A61N 1/36046 |
| 2017/0049619 A1 | 2/2017 | Kahook |
| 2017/0239459 A1 | 8/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368333 A1 | 12/2017 | Loudin et al. |
| 2017/0368359 A1 | 12/2017 | Loudin et al. |
| 2018/0064940 A1 | 3/2018 | Ackermann et al. |
| 2018/0064941 A1 | 3/2018 | Ackermann et al. |
| 2018/0064942 A1 | 3/2018 | Franke et al. |
| 2018/0153394 A1 | 6/2018 | Franke et al. |
| 2018/0154137 A1 | 6/2018 | Ackermann et al. |
| 2018/0154161 A1 | 6/2018 | Ackermann et al. |
| 2018/0161579 A1 | 6/2018 | Franke et al. |
| 2018/0280688 A1 | 10/2018 | Loudin et al. |
| 2019/0022392 A1 | 1/2019 | Franke et al. |

FOREIGN PATENT DOCUMENTS

| | | |
|---|---|---|
| CN | 101503491 A | 8/2009 |
| CN | 101589085 A | 11/2009 |
| CN | 101939043 A | 1/2011 |
| CN | 102266592 A | 12/2011 |
| CN | 103467652 A | 12/2013 |
| DE | 102006048819 A1 | 4/2008 |
| EP | 0109935 A1 | 5/1984 |
| EP | 1497483 | 1/2005 |
| EP | 1651307 | 5/2006 |
| EP | 1919553 | 5/2008 |
| EP | 1958661 A1 | 8/2008 |
| EP | 2205193 | 7/2010 |

(56) References Cited

FOREIGN PATENT DOCUMENTS

| | | |
|---|---|---|
| EP | 2205314 | 7/2010 |
| EP | 2102681-0001 | 10/2012 |
| EP | 2199000-0001 | 3/2013 |
| EP | 3263175 A1 | 1/2018 |
| GB | 2 129 690 B | 3/1987 |
| GB | 2 456 002 A | 7/2009 |
| JP | S60500241 A | 2/1985 |
| JP | 2002-519138 A | 7/2002 |
| JP | 2002-325851 A | 11/2002 |
| JP | 2002-539859 A | 11/2002 |
| JP | 2004526510 A | 9/2004 |
| JP | 2005-052461 A | 3/2005 |
| JP | 2005-144178 A | 6/2005 |
| JP | 2005521489 A | 7/2005 |
| JP | 2006-515900 A | 6/2006 |
| JP | 2006-311917 A | 11/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2009-523503 A | 6/2009 |
| JP | 2010-505563 A | 2/2010 |
| JP | 2010-051562 A | 3/2010 |
| JP | 2010506654 A | 3/2010 |
| JP | 2010-537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| WO | WO-00/01320 A2 | 1/2000 |
| WO | WO-00/56393 A1 | 9/2000 |
| WO | WO-00/62672 A1 | 10/2000 |
| WO | WO-02/078592 A2 | 10/2002 |
| WO | WO-03/082080 A2 | 10/2003 |
| WO | WO-2003/087433 A1 | 10/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |

OTHER PUBLICATIONS

Amparo (2013). "Topical Interleukin 1 Receptor Antagonist for Treatment of Dry Eye Disease," JAMA Ophth. 131(6):E1-E9.

Bajpai et al. (2012). "Preparation, Characterization and Water Uptake Behavior of Polysaccharide Based Nanoparticles," Prog. Nanotech. Nanomat. 1(1):9-17.

Baraniuk et al. (2007). "Nasonasal Reflexes, the Nasal Cycle, and Sneeze," Curr. Allergy and Asthma Reports 7:105-111.

Baroody FM, Foster KA, Markaryan A, et al. Nasal ocular reflexes and eye symptoms in patients with allergic rhinitis. Ann Allergy Asthma Immunol 2008;100:194-199.

Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009;123:1342-1348.

Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.

Calonge (2001). "The Treatment of Dry Eye," Survey Ophth. 45(2)S227-S239.

Cipriano et al. (2014). "Superabsorbent Hydrogels That Are Robust and Highly Stretchable," Am. Chem Soc. 47(13):4445-4452.

Corrected Notice of Allowance dated Feb. 23, 2015, for U.S. Appl. No. 14/256,915, filed Apr. 18, 2014, 2 pages.

Dart et al. (2002). "Effects of 25% Propylene Glycol Hydrogel (Solugel) on Second Intention Wound Healing in Horses," Vet. Surg. 31(4):309-313.

Drummond PD. Lacrimation and cutaneous vasodilatation in the face induced by painful stimulation of the nasal ala and upper lip. J Auton Nerv Syst 1995;51:109-16.

Elsby et al. (1967). "Lacrimal Secretion in the Cat," Br. J. Pharm. Chemother. 29(1):1-7.

Extended European Search Report (includes Supplementary European Search Report and Search Opinion) received for European Patent Application No. 11842076.9, dated Oct. 10, 2014.

Extended European Search Report dated Nov. 18, 2016, for EP Application No. 14 785 631.4, filed on Apr. 18, 2014, 7 pages.

Final Office Action received for U.S. Appl. No. 14/256,916, dated Apr. 8, 2015, 16 pages.

Final Office Action received for U.S. Appl. No. 14/313,937 dated Apr. 29, 2015, 13 pages.

Final Office Action received for U.S. Appl. No. 14/630,471, dated Sep. 26, 2016, 22 pages.

Final Office Action received for U.S. Appl. No. 14/256,916, dated Aug. 19, 2016, 19 pages.

Final Office Action dated Sep. 23, 2016, for U.S. Appl. No. 14/809,109, filed Jul. 24, 2015, 10 pages.

Final Office Action dated Feb. 1, 2017, for U.S. Appl. No. 14/920,852, filed Oct. 22, 2015, 20 pages.

Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.

Gupta et al. (1997). "Nasolacrimal Stimulation of Aqueous Tear Production," Cornea 16(6):645-648.

Heigle TJ, Pflugfelder SC. Aqueous tear production in patients with neurotrophic keratitis. Cornea 1996;15:135-8.

Holzer P. Capsaicin: cellular targets, mechanisms of action, and selectivity for thin sensory neurons. Pharmacol Rev 1991;43:143-201.

(56) References Cited

OTHER PUBLICATIONS

Ikemura et al. (2008). "UV-VIS Spectra and Photoinitiation Behaviors of Acylphosphine Oxide and Bisacylphosphine Oxide Derivatives in unfilled, Light-Cured Dental Resins," Dental Mat. J. 27(6):765-774.
International Preliminary Report on Patentability received for PCT Patent Application No. PCT/US2011/060989, dated May 30, 2013.
International Preliminary Report on Patentability received for PCT Patent Application No. PCT/US2012/032629, dated Oct. 17, 2013.
International Preliminary Report on Patentability received for PCT Patent Application No. PCT/US2014/034733, dated Oct. 29, 2015.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report received for PCT Patent Application No. PCT/US2015/57021, dated Feb. 10, 2016.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action received for U.S. Appl. No. 14/816,846, dated Sep. 11, 2015, 5 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S. Appl. No. 14/313,937, dated Oct. 6, 2015, 7 pages.
Non-Final Office Action Received for U.S. Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016.
Zilstorff-Pedersen (1965). "Quantitative Measurements of the Nasolacrimal Reflex," Arch. Oto. 81:457-462.
Olsen et al. (1998) "Human Sclera: Thickness and Surface Area." American Journal of Ophthalmology. Feb. 1998, vol. 125, Issue 2, pp. 237-241.
"Vapor Pressure Data for H2O" (2012). Handbook of Chemistry and Physics, 73rd edition, 1 total page.
Anonymous (2007). "The epidemiology of dry eye disease: report of the Epidemiology Subcommittee of the International Dry Eye WorkShop (2007)," Ocul. Surf. 5(2):93-107.
Eye Health (2014). "Watery eyes in cold weather," Oregon Eye Specialists, PC, located at http://www.oregoneyes.net/watery-eyes-in-cold-weather/, 3 total pages.
Friedman et al. (2016). "A nonrandomized, open-label study to evaluate the effect of nasal stimulation on tear production in subjects with dry eye disease," Clin. Ophthal. 10:795-804.
Friedman, N. J. (2010) "Impact of Dry Eye Disease and Impact on Quality of Life." Current Opinion in Ophthalmology. 21:310-316.
Galor, A. et al. (2014). "Environmental factors affect the risk of dry eye syndrome in a United States veteran population," Opth. 121:972-973.
Harvard Health Publishing (2010). "Dry eyes and what you can try," Harvard Medical School, 2 total pages.
McDonald et al. (2009) "Hydroxypropyl Cellulose Ophthalmic Inserts (Lacrisert) Reduce the Signs and Symptoms of Dry Eye Syndrome and Improve Patient Quality of Life", Transactions of the American Ophthalmological Society, 107:214-222.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Van Setten, G. et al. (2016). "Evidence of seasonality and effects of psychrometry in dry eye disease," Acta Opth. 94:499-506.

(56) References Cited

OTHER PUBLICATIONS

Yu, et al. (Apr. 2011) "The Economic Burden of Dry Eye Disease in the United States: a Decision Tree Analysis", Cornea, 30(4):379-387.

* cited by examiner

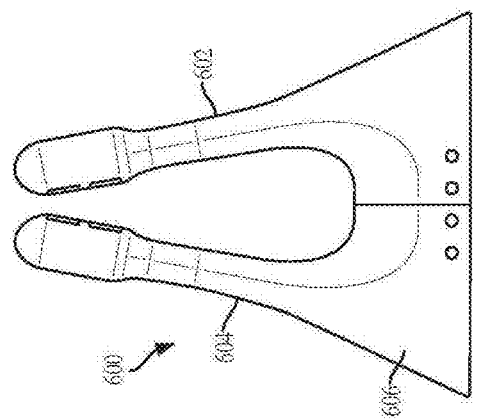
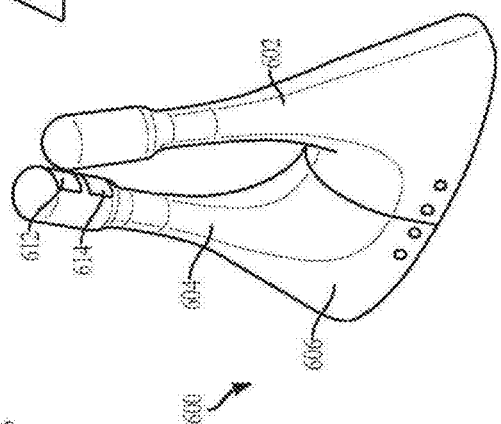
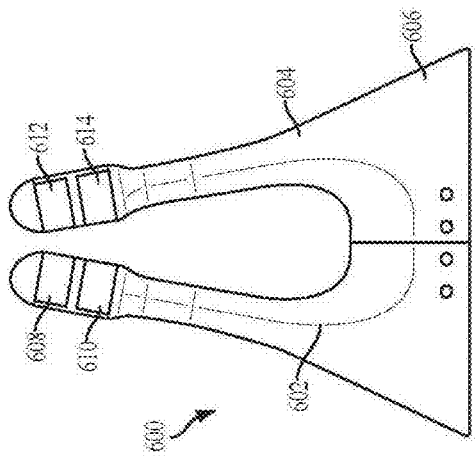

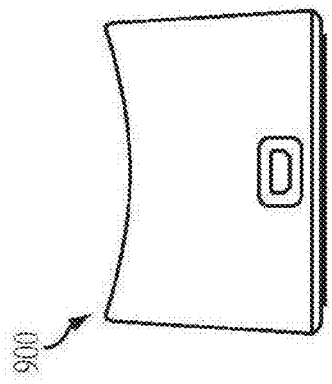
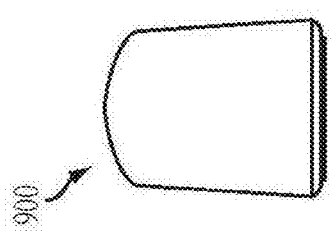
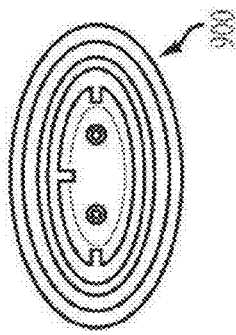
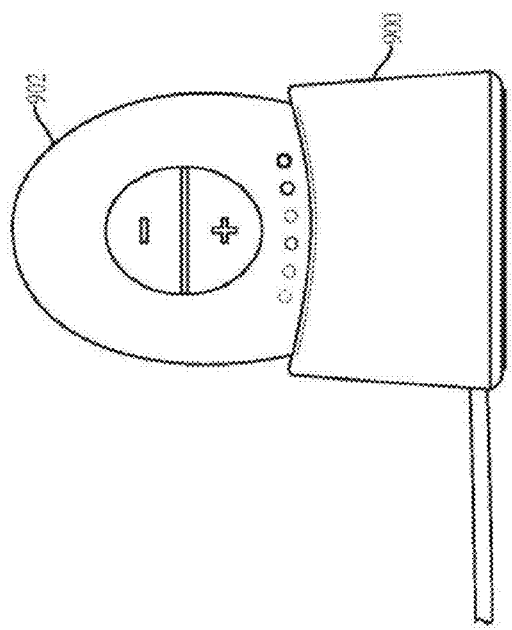
FIG. 9C
FIG. 9D
FIG. 9B
FIG. 9A

INTRANASAL STIMULATION FOR ENHANCED RELEASE OF OCULAR MUCINS AND OTHER TEAR PROTEINS

CROSS-REFERENCE TO RELATED APPLICATIONS

This application claims priority to U.S. Provisional Application No. 62/263,498 filed on Dec. 4, 2015; U.S. Provisional Application No. 62/321,170 filed on Apr. 11, 2016; U.S. Provisional Application No. 62/330,744 filed on May 2, 2016; and U.S. Provisional Application No. 62/376,834 filed on Aug. 18, 2016. Each of the foregoing disclosures is hereby incorporated by reference in its entirety.

FIELD

Described herein are devices and methods for increasing ocular mucin and other tear protein release using intranasally delivered electrical stimulation. The devices may deliver electrical stimulation to the nasal mucosa to trigger degranulation of conjunctival goblet cells, which in turn releases secretory mucins into the tear fluid. The intranasal stimulation may also trigger release of lysozyme, lactoferrin, and other tear proteins into the aqueous layer of the tear film. The methods may further comprise obtaining feedback relating to the efficacy of the delivered electrical stimulation by measuring impedance or an electromyogram (EMG) signal.

BACKGROUND

Dry eye is thought to stem from abnormalities of the tear film on the surface of the eye. The tear film includes three layers, an inner mucus layer, an outer lipid layer, and an aqueous layer between them. The mucus layer, which is primarily composed of mucins, is the thinnest layer and functions to adhere the tear film to the eye.

Mucins are high molecular weight glycoproteins that have various functions. Some mucins are secreted into the mucous layer while others form the glycocalyx (transmembrane mucins), which is the specific structure that adheres the tear film to the eye. The glycocalyx is partially embedded in the lipid bilayer of corneal and conjunctival epithelial cells and forms a hydrophilic network that binds secreted mucins in the mucus layer to these cells. Additionally, the mucins in the mucus layer and glycocalyx are believed to attract water, thereby decreasing the surface tension of the tear film and facilitating the even spread of the aqueous layer on the eye, which in turn may protect the eye from pathogens and make the ocular surface less susceptible to damage. Mucins that have been detected in the tear film include MUC1, MUC2, MUC4, MUC5AC, MUC7, MUC13, MUC15, MUC16, and MUC 17. Transmembrane mucins include MUC1, MUC4, MUC13, MUC15, MUC16, and MUC17. Secreted mucins include MUC2, MUC5AC, and MUC7, which can be further classified as gel-forming or soluble. MUC5AC has been identified as a secreted, gel-forming mucin. Mucins found on the ocular surface are primarily produced by goblet cells (e.g., secreted mucin MUC5AC), apical cells of the conjunctiva and cornea (e.g., transmembrane mucins MUC1, MUC2 and MUC4), and the lacrimal gland (e.g., secreted mucin MUC7). In addition to mucins, the lacrimal gland secretes proteins into the aqueous layer that promote spreading of the tear film and that help maintain a healthy environment on the ocular surface. Exemplary proteins include lysozyme, lactoferrin, tear specific prealbumin, caeruloplasmin, lacitin, lipophilin, and immunoglobulins A, D, G, and E.

Decreased mucin and tear protein levels have been associated with dry eye. Common treatment approaches are typically palliative in nature, attempting to supplement the patient's natural tears or improve the residence time of the limited tear volume already present on the ocular surface (Dry Eye Workshop 2007. The Epidemiology of Dry Eye Disease. Ocul. Sur. 2007; 5(2): 93-107). These treatment approaches have had limited success. It would therefore be desirable to have an improved treatment that increases mucin and other tear protein levels in the tear film.

SUMMARY

Described herein are devices and methods for increasing mucin release on the ocular surface of a subject. The devices may be stimulator devices configured to contact the nasal mucosa and intranasally deliver an electrical stimulus. In some instances, the stimulator devices are configured as handheld stimulators. The electrical stimulus is capable of increasing the mucin concentration in the tear film by, e.g., triggering degranulation of goblet cells in the conjunctiva of the eye.

The methods for increasing mucin on an ocular surface of a subject generally comprise intranasally delivering an electrical stimulation to the subject, and stimulating release of an ocular mucin, where the released ocular mucin improves a condition of the eye. The intranasally delivered electrical stimulation may be delivered for at least 10 seconds, and in some instances, for at least three minutes, and may be repeated as desired. The electrical stimulation is generally intranasally delivered to the nasal mucosa. Additionally or alternatively, the intranasal delivery of electrical stimulation may include delivering an electrical stimulus comprising a waveform having on and off periods.

Electrical stimulation may be intranasally delivered using a stimulator, where the stimulator comprises a stimulator body and a stimulator probe, and further where the stimulator probe comprises at least one nasal insertion prong. A portion of the nasal insertion prong may be placed in contact with the nasal mucosa as part of the stimulation delivery process. The nasal insertion prong may include various types of electrodes, however, it may be useful for the electrode to comprise a hydrogel. The stimulator body may be sized for holding in one hand. Some variations of the stimulator probe may include two nasal insertion prongs. In these variations, the two nasal insertion prongs may be biased toward each other, and the bias used to promote stimulation of the septum of the nasal cavity and/or to hold the stimulator in the nose during intranasal delivery of the electrical stimulation.

The intranasally delivered electrical stimulation may stimulate release of an ocular mucin. Exemplary ocular mucins include without limitation, MUC1, MUC2, MUC4, MUC5AC, MUC7, MUC13, MUC15, MUC16, and MUC 17. Some of these mucins, e.g., MUC5AC, may be released by stimulating degranulation of goblet cells. Various parameters of the electrical stimulation waveforms may be tailored to achieve goblet cell degranulation or release of a particular type of ocular mucin from other cells, e.g., apical cells or acinar cells. In some instances, intranasal stimulation may decrease the concentration of certain inflammatory mediators in the tear film.

The intranasally delivered electrical stimulation may also be used in methods that increase the release of tear proteins in the aqueous layer of the tear film or the concentration of tear proteins in the aqueous layer of the tear film. These tear proteins include without limitation, lysozyme, lactoferrin, tear specific prealbumin, caeruloplasmin, lacitin, lipophilin, and immunoglobulins A, D, G, and E.

The methods for increasing mucin and other tear proteins on the ocular surface may further include identifying an optimal stimulation location for intranasally delivering the electrical stimulation. The optimal stimulation location may be identified via impedance monitoring. Additionally or alternatively, the optimal stimulation location may be identified by obtaining feedback from an electromyogram (EMG) signal from a facial muscle near the nose, cheeks, or around the eyes. The impedance and EMG signals may be measured intranasally using the same device that delivers the electrical stimulation. In other instances, the impedance and EMG signals are measured by an extranasal device. One or more parameters of the electrical stimulation waveforms may be tailored or optimized to achieve release of the tear proteins from secretory vesicles of the lacrimal gland.

Methods for treating dry eye are also described herein. The methods generally include intranasally delivering electrical stimulation to a subject afflicted with dry eye; obtaining feedback relating to the efficacy of the delivered electrical stimulation by measuring impedance or an electromyogram (EMG) signal from a facial muscle near the nose, cheeks, or around the eyes of the subject; formulating a treatment plan based on the feedback; and continuing intranasal delivery of the electrical stimulation according to the treatment plan, where the delivered electrical stimulation increases the release of a tear protein to treat the dry eye of the subject. The tear protein can be mucin, lysozyme, lactoferrin, tear specific prealbumin, caeruloplasmin, lacitin, lipophilin, and immunoglobulins A, D, G, and E, or a combination thereof.

Additionally or alternatively, the methods for treating dry eye may include determining whether a subject afflicted with dry eye is deficient in a tear protein on an ocular surface, and based on the tear protein found to be deficient, intranasally delivering an electrical stimulation to the subject, where one or more parameters of the intranasally delivered electrical stimulation is selected based upon the deficient tear protein, and where the intranasally delivered electrical stimulation is effective to increase the release or the concentration of the deficient tear protein on the ocular surface. The tear protein can be mucin, lysozyme, lactoferrin, tear specific prealbumin, caeruloplasmin, lacitin, lipophilin, and immunoglobulins A, D, G, and E, or a combination thereof. In some instances, the methods may include determining a type of dry eye in a subject and intranasally delivering to the subject an electrical stimulation according to a treatment plan based on the determined type of dry eye, e.g., mild dry eye, moderate dry eye, or severe dry eye.

Intranasally delivered electrical stimulation and release of ocular mucins and other tear proteins may improve dry eye and ocular inflammation, as well as other ocular conditions. The methods described herein may further be combined with additional treatments, such as the application of artificial tears to the ocular surface, use of one or more punctum plugs, and/or the application of an active agent to the ocular surface. Here, for example, the active agent may comprise one more antibacterial agents, one or more anti-inflammatory agents, one or more antihistamines, one or more steroids, or combinations thereof.

BRIEF DESCRIPTION OF THE DRAWINGS

FIGS. 6A, 6B, and 6C depict back, front, and perspective views, respectively, of an exemplary stimulator probe suitable for the stimulators described here.

FIGS. 9A-9D depict portions of an exemplary stimulator system comprising a stimulator and a base station. FIG. 9A shows a front view of the stimulator body docked in the base station, while FIGS. 9B, 9C, and 9D depict side, back, and top views, respectively, of the base station.

DETAILED DESCRIPTION

Described here are devices and methods for increasing tear protein release using intranasal stimulation. Tear proteins include mucins, which are secreted into the mucin layer of the tear film, and proteins secreted by the lacrimal gland into the aqueous layer of the tear film. In some variations, the devices and methods are configured to deliver an electrical stimulus to the nasal mucosa to cause mucin release, e.g., by stimulating degranulation of goblet cells. Increased mucin production may be useful in 1) adhering the tear film to the ocular surface; 2) enhancing lubrication of the ocular surface; 3) preventing break-up of the tear film; 4) capturing dust, allergens, and bacteria, which in turn may reduce the sensory input that drives the inflammatory/histamine response in the eye; and 5) preventing desiccation of corneal and/or conjunctival epithelial cells. In other variations, the devices and methods are configured to deliver an electrical stimulus to the nasal mucosa to cause secretion of other tear proteins from the lacrimal gland into the aqueous layer of the tear film, e.g., lysozyme, lactoferrin, tear specific prealbumin, caeruloplasmin, lacitin, lipophilin, and immunoglobulins A, D, G, and E. Increased tear protein secretion may be useful in promoting spreading of the tear film and controlling infectious agents on the ocular surface, as well as and regulating the osmotic balance of the ocular surface.

Figure 1:
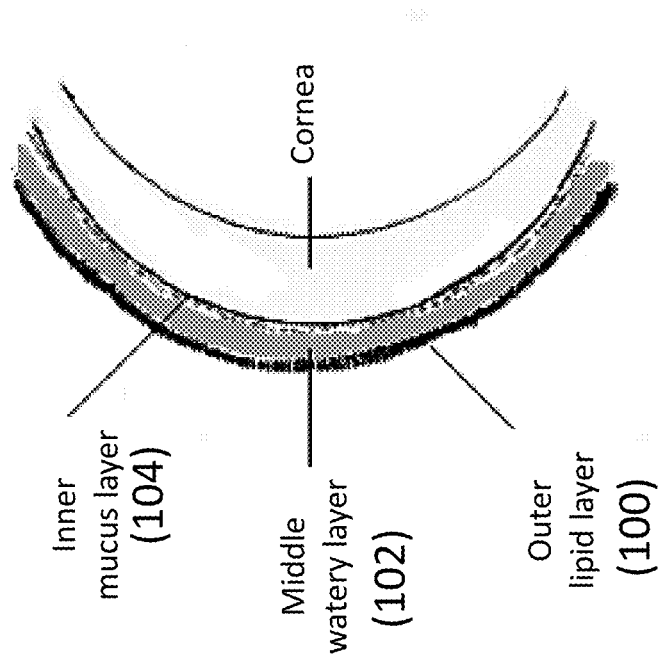
FIG. 1 is a schematic diagram showing the layers of the tear film on the corneal surface.

The tear film maintains the transparency and health of the cornea, and is generally comprised of three layers, including an outer lipid layer 100, a middle aqueous layer 102, and an inner mucus layer 104, as shown in FIG. 1, although it may also be thought as having a surface lipid component and then phases of aqueous with differing concentrations of mucins suspended throughout. Regardless, the tear film in its entirety provides a smooth optical interface needed for good visual acuity, supplies nutrients to the eye and flushes away waste products, and helps to protect against shear forces generated when blinking and during eye movements, as well as protects against environmental exposure and foreign bodies.

Figure 2:
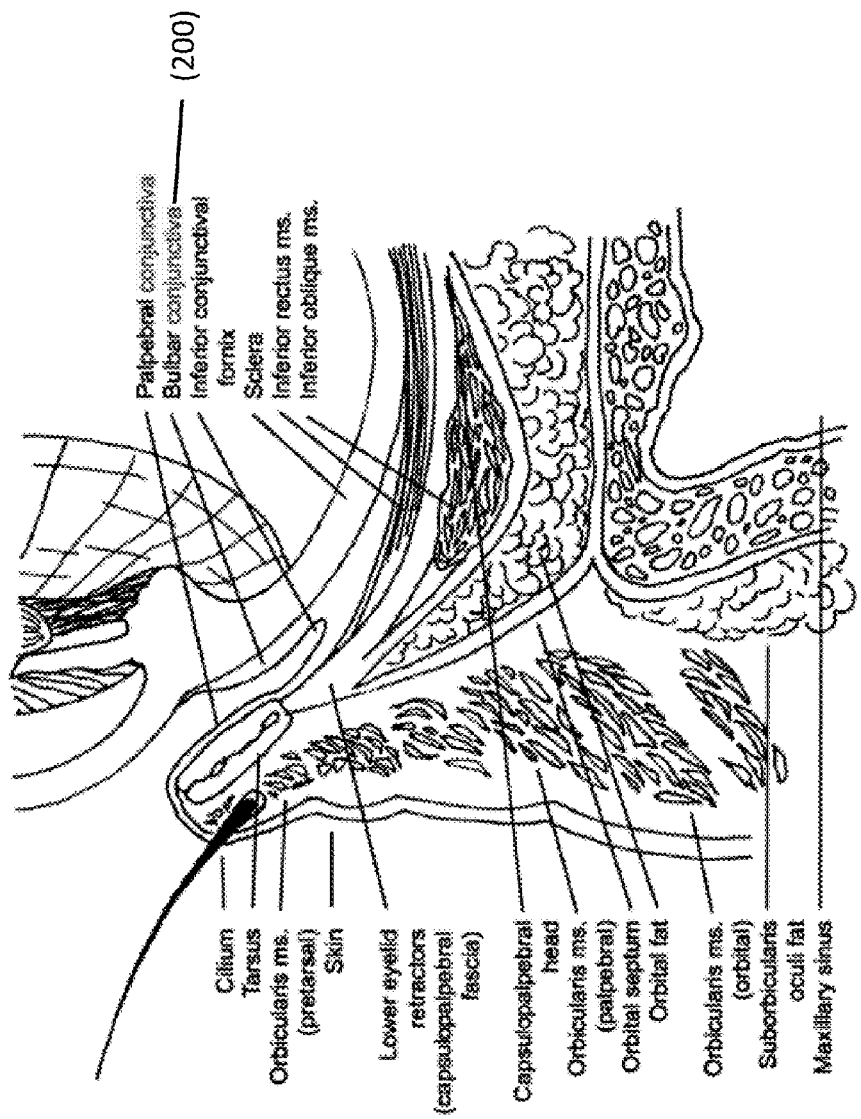
FIG. 2 illustrates the anatomy of the lower eyelid, eye, and conjunctiva.
Figure 3:
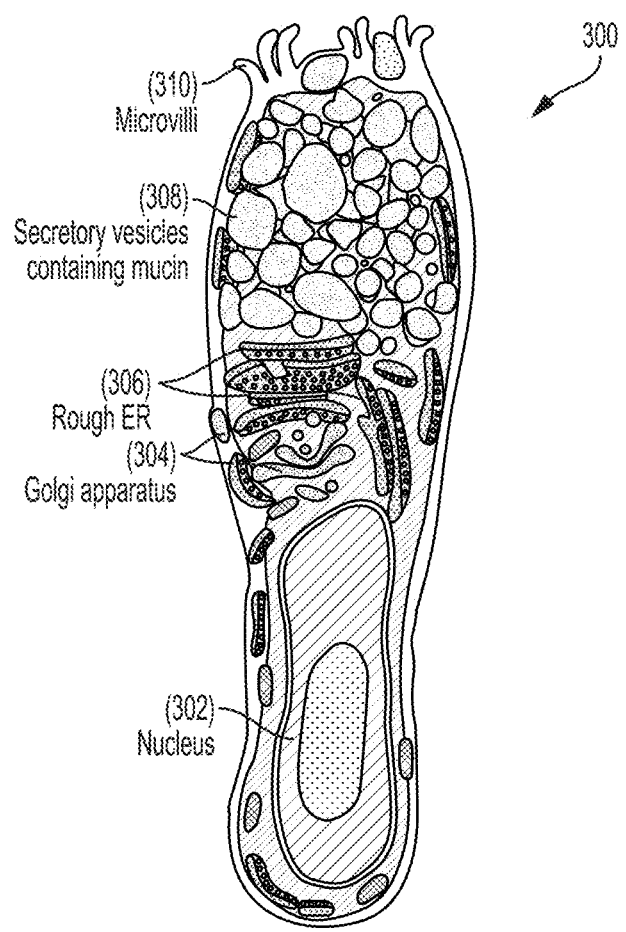
FIG. 3 is a schematic diagram of a goblet cell.
Figure 4A:
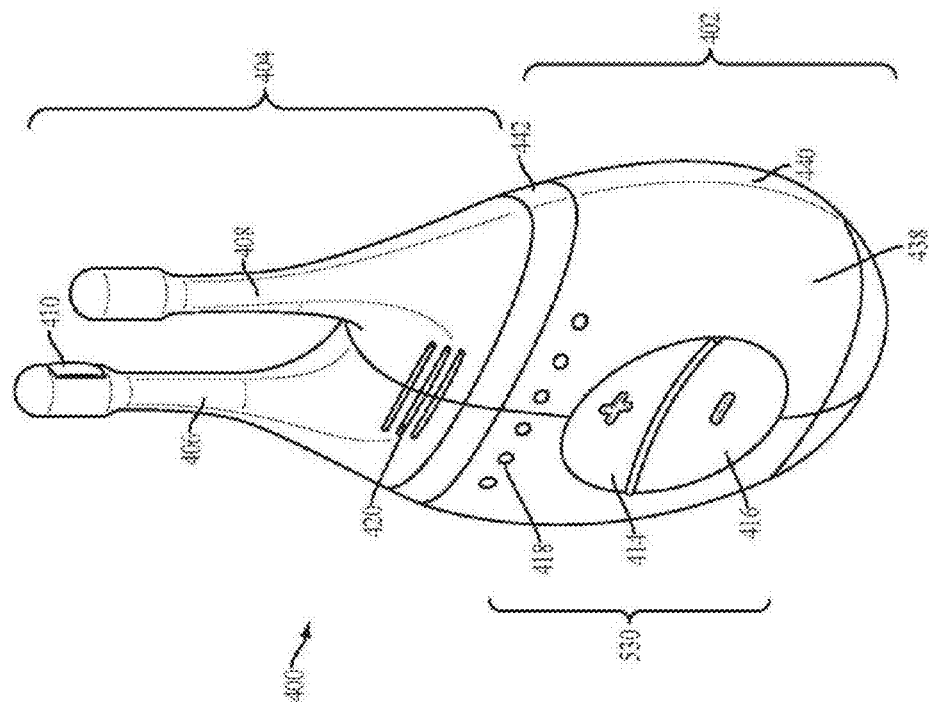
FIGS. 4A, 4B, 4C, 4D, 4E show perspective, front, back, cut-away back, and cut-away side views, respectively, of an illustrative variation of a stimulator.
Figure 4C:
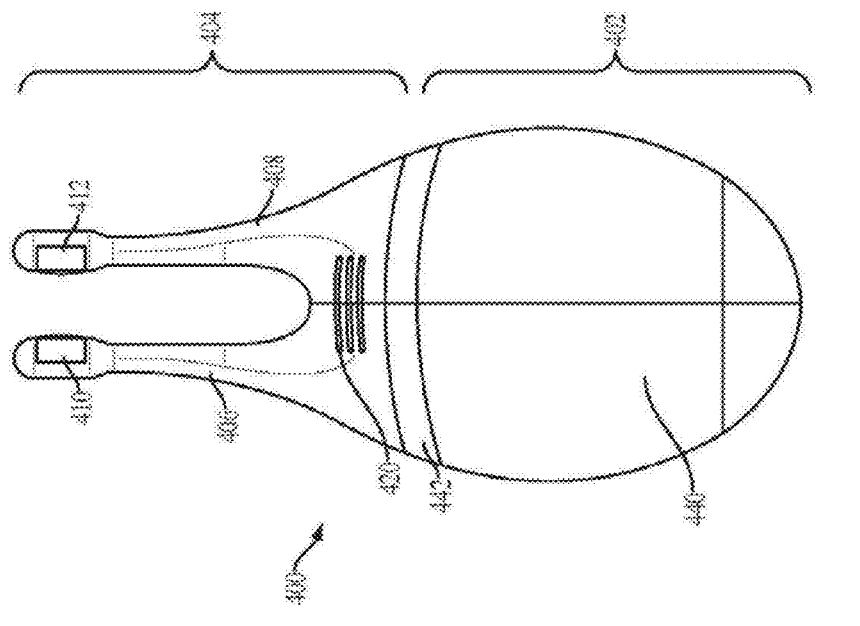
Figure 4B:
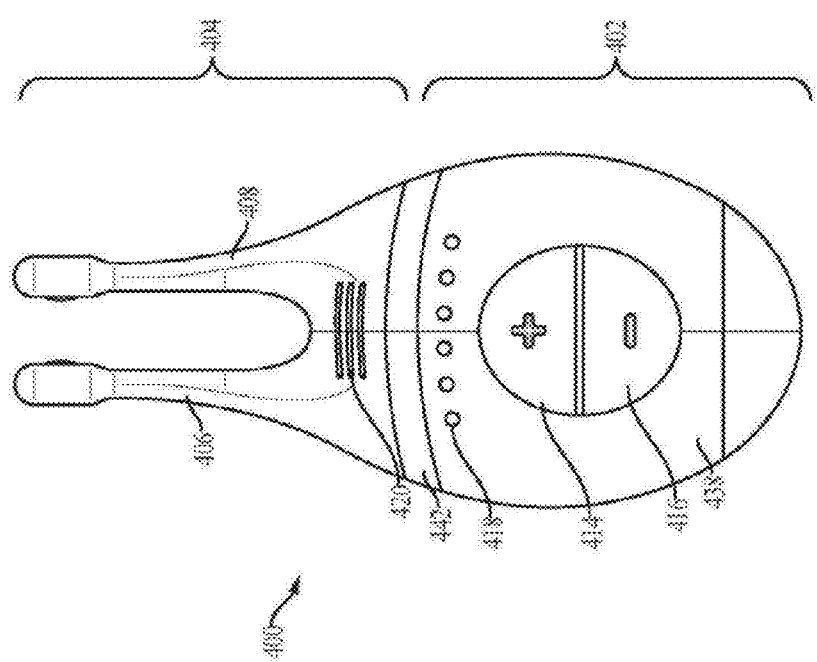
Figure 4E:
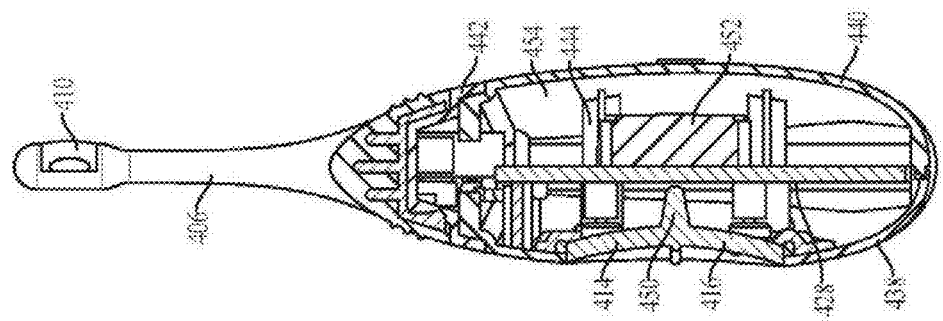
Figure 4D:
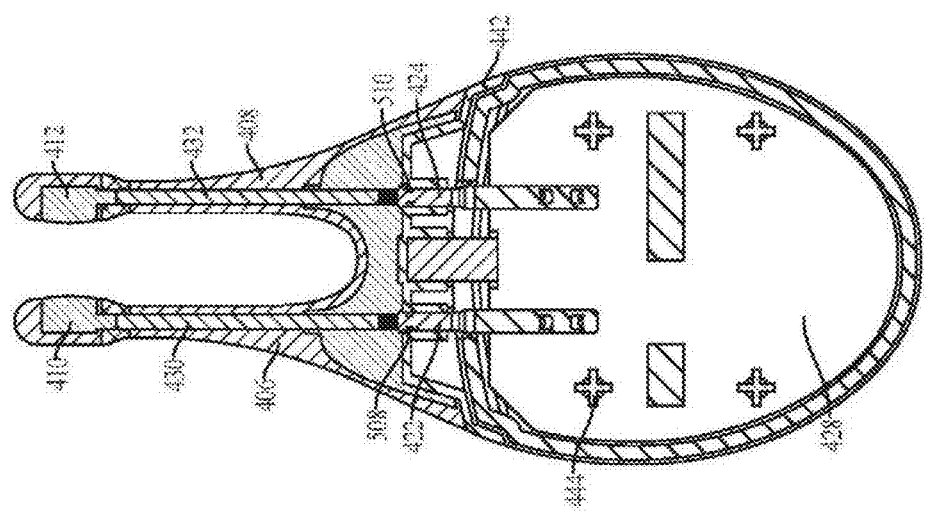

The inner mucus layer is primary comprised of mucins. Goblet cells, which are modified simple columnar epithelial cells found in the conjunctiva of the eye (e.g., bulbar conjunctiva 200 shown in FIG. 2), produce secretory mucins such as MUC5AC. Other types of mucins are produced by acinar cells of the lacrimal gland and apical cells of the conjunctiva and cornea. Referring to FIG. 3, goblet cell 300 has a nucleus 302 and organelles, e.g., Golgi apparatus 304 and rough endoplasmic reticulum 306 at the base of the cell. Secretory vesicles/granules containing mucin 308 are contained within the top portion of the cell, and give the cell its goblet shape when the granules 308 expand. Microvilli 310 at the cell tip increase the surface area of the cell for secretion.

In patients with dye eye, the proper amount of mucins in the tear film may be lacking. The abnormal mucin production may be due to systemic diseases (e.g., Sjögren's syndrome), medications, or other causes. In some variations, the methods described herein may use application of intranasal stimulation to increase mucin release into the tear film. Additionally or alternatively, the methods described herein may use intranasal stimulation to increase mucin release by triggering goblet cell degranulation (i.e., release of mucin-containing vesicles/granules).

Intranasal stimulation may in part increase mucin secretion through modulating parasympathetic innervation of goblet cells in the conjunctiva. More particularly, afferent parasympathetic stimulation with particular waveforms (described in detail elsewhere herein) may increase the secretory drive of goblet cells. In some variations, intranasal stimulation may increase mucin release by stimulating the pterygopalatine ganglion (PPG) via the greater petrosal nerve. In other variations, repeated and/or sustained intranasal stimulation over a period of time may improve release of mucin from goblet cells (goblet cell degranulation) and/or increase the number/density of goblet cells in the conjunctiva.

Devices and Systems

Figure 5:
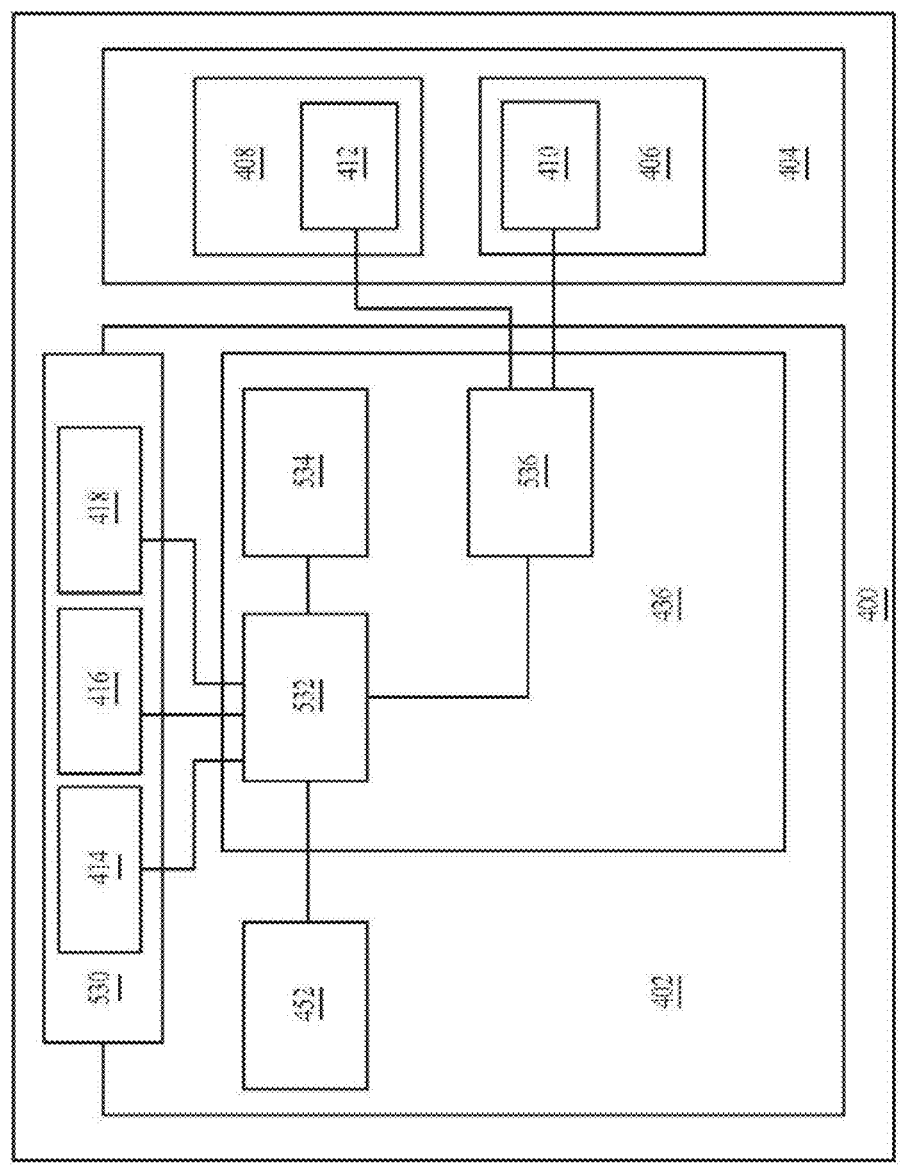
FIG. 5 shows a block diagram schematically representing a variation of a stimulator.

Generally, the devices and methods described herein may comprise a stimulator configured to deliver an electrical stimulus to the inner cavity of the nose. The instrument consists of four distinct parts: 1) A reusable base unit, which produces the electrical stimulation waveform, 2) A disposable tip assembly that inserts into the nasal cavity and stimulates the target intranasal tissue, 3) A reusable cover to protect the tip assembly, 4) A charger, which recharges the battery inside the base unit. Some variations of the stimulation systems described here may comprise a handheld stimulator. FIGS. 4A, 4B, 4C, 4D, 4E show perspective, front, back, cut-away back, and cut-away side views, respectively, of an illustrative variation of a handheld stimulator 400, respectively. FIG. 5 shows a block diagram schematically representing the stimulator 400. As shown in FIGS. 4A-4E, the stimulator 400 may comprise a stimulator body 402 and a stimulator probe 404. Generally, the stimulator body 402 may be configured to generate a stimulus that may be delivered to the subject. The stimulator body 402 may comprise a front housing 438, back housing 440, and proximal housing 442, which may fit together to define a body cavity 454. The body cavity 454 may contain a control subsystem 436 and a power source 452, which together may generate and control the stimulus.

The stimulator body 402 may comprise a user interface 530 comprising one or more operating mechanisms to adjust one or more parameters of the stimulus. The operating mechanisms may provide information to the control subsystem 436, which may comprise a processor 532, memory 534, and/or stimulation subsystem 536. In some variations, the operating mechanisms may comprise first and second buttons 414 and 416. In some variations, pressing the first button 414 may turn on the stimulator and/or change one or more parameters of the stimulus (e.g., increase the intensity of the stimulus, change the stimulation pattern, or the like), while pressing the second button 416 may turn off the stimulator and/or change one or more parameters of the stimulus (e.g., decrease the intensity of the stimulus, change the stimulation pattern, or the like). Additionally or alternatively, the user interface may comprise one or more feedback elements (e.g., based on light, sound, vibration, or the like). As shown, the user feedback elements may comprise light-based indicators 418, which may provide information to the user, as described in more detail below.

In the variation shown in FIGS. 4A-4E, the user interface may be configured for use by the subject receiving the intranasal stimulation. However in other variations, the stimulators may comprise an interface configured for use by a person other than the subject receiving the intranasal stimulation, such as a medical professional. For example, a stimulator may comprise a remote interface operable at a distance from the stimulator body. The remote interface may be connected to the stimulator body wirelessly or in a wired manner (e.g., via a cable). The remote interface may allow the stimulator to be turned on/off and or may be used to change one or more parameters of the stimulation. A remote interface may be desirable, for example, so a medical professional can adjust the stimulus parameters when intranasal stimulation is delivered at the medical professional's office. In some variations, the stimulators may be configured to be controlled by both the subject receiving the intranasal stimulation and another person (e.g., a medical professional). For example, a stimulator may comprise a user interface on the stimulator body, as shown in FIGS. 4A-4E, and a remote interface.

The stimulus may be delivered to a subject via the stimulator probe 404. In some variations the stimulator body 402 and stimulator probe 404 may be reversibly attachable. Some or all of the stimulator 400 may be disposable. For example, in some variations the stimulator body may be permanently attached to the stimulator probe, and the entire stimulator may be disposable. In other variations, one or more portions of the stimulator 400 may be reusable. For example, in variations where the stimulator probe 404 is releasably connected to the stimulator body 402, the stimulator body 402 may be reusable, and the stimulator probe 404 may be disposable and periodically replaced.

The stimulator probe 404 may comprise at least one nasal insertion prong, which may be configured to be at least partially inserted into the nasal cavity of a subject. In the handheld stimulator variation shown in FIGS. 4A-4E, the stimulator probe 404 may comprise two nasal insertion prongs 406 and 408. The stimulator probe 404 may further comprise ridges 420, which may allow the subject to more easily grip the probe 404. Each nasal insertion prong may comprise at least one electrode. As shown, the probe 404 may comprise a first electrode 410 on nasal insertion prong 406 and a second electrode 412 on nasal insertion prong 408. As shown in the cut-away view of the stimulator 400 in FIG. 4D, the electrodes 410 and 412 may be connected to leads 430 and 432 located within prongs 406 and 408, respectively. The leads 430 and 432 may in turn be connected to connectors 422 and 424, respectively. Connectors 422 and 424 may extend through lumens 508 and 510 in the proximal housing 442, and may connect directly or indirectly to the control subsystem 436 and power source 452. As such, the electrical stimulus may travel from the control subsystem 436 through the connectors 422 and 424, through the leads 430 and 432, and through the electrodes 410 and 412.

In some variations, the nasal insertion prongs may be parallel when not inserted into the nose of a subject, but may have sufficient flexibility to allow the prongs to self-align to the desired stimulation location when inserted into a user's nasal cavities. In other variations of stimulators comprising two nasal insertion prongs, however, the nasal insertion prongs may not be parallel to each other when not inserted into the nose of a subject; that is, the nasal insertion prongs may be positioned at an angle relative to each other. For example, FIGS. 6A-6C show stimulator probe 600 comprising first and second nasal insertion prongs 602 and 604, respectively, connected to a base member 606. The nasal insertion prongs 602 and 604 may be connected to the base member 606 such that they are angled toward each other. In some variations, the angle between the nasal insertion prongs may be adjustable. For example, the nasal insertion prongs may be biased toward a configuration in which the nasal insertion prongs are at an angle relative to each other, but may be movable to a parallel configuration. When the prongs are inserted into nasal cavities to position tissue (e.g., a nasal septum) between the prongs, the prongs may be rotated away from each other prior to insertion into the nasal cavities. Once positioned in the nasal cavities, the force may be removed and the return bias may rotate the prongs toward each other, and the return bias of the stimulator probe may press the distal ends of the nasal insertion prongs against tissue. This may help to increase electrode apposition with tissue, and in some instances may act to hold the stimulator probe in place relative to tissue. To remove the stimulator probe from tissue, the prongs may again be rotated away from each other to release the tissue positioned between the prongs.

In some variations in which the stimulator comprises two nasal insertion prongs biased toward each other, the return bias may be sufficient to hold the stimulator in place. In these variations, once positioned in the nasal cavities, the distal ends of the nasal insertion prongs may press against tissue with sufficient force to allow for hands-free use—that is, the user may not need to hold the stimulator in order for the electrodes to remain in apposition with the target tissue. This may improve ease of use. In other variations, the return bias may be sufficient to reduce unintended movement of the nasal insertion prongs while inserted, while still requiring the stimulator to be held.

The devices (and systems) described herein may additionally or alternatively also comprise other features to allow hands-free or reduced-handling use. For example, the system may comprise a strap configured to be placed around a user's head and attached to the stimulator to hold the stimulator in place during stimulation. The strap may be removably attachable to the stimulator, or in other variations may be permanently attached to the stimulator. In some variations of stimulators configured for hands-free use, the stimulators may be configured to be inserted and/or removed by a user. In other variations, the stimulators may be configured to be inserted/removed by a medical professional.

Figure 7:
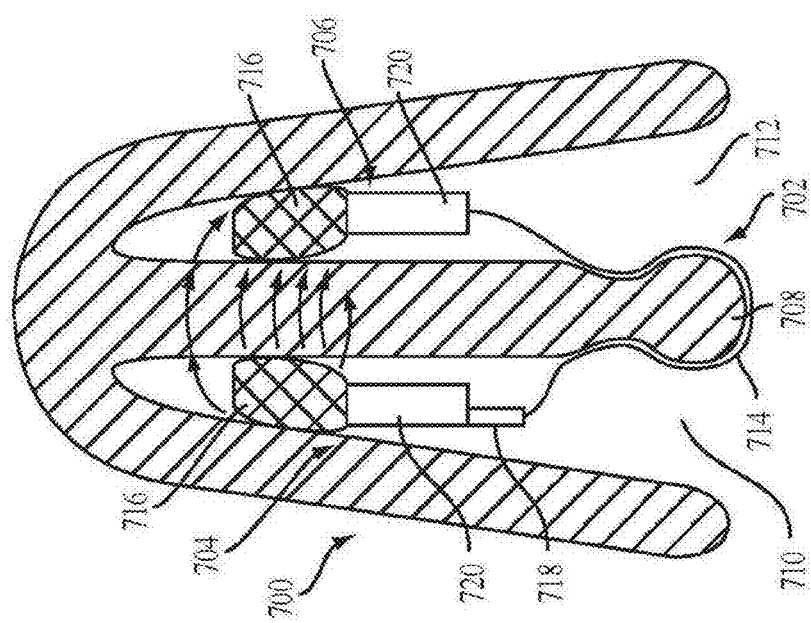
FIG. 7 shows a cross-sectional view of an exemplary stimulator positioned in the nasal cavities.

For example, FIG. 7 depicts a cross-sectional view of a subject's nose having a septum 708 and nostrils 710 and 712 having a variation of a hands-free stimulator 700 located therein. As shown there, the stimulator 700 may comprise a clip 702, a first stimulator unit 704 attached to a first end of the clip 702, and a second stimulator unit 706 attached to a second end of the clip 702. Generally, the clip 702 may be configured to temporarily connect the stimulator 700 to a nasal septum 708 of a subject, which may position the first stimulator unit 704 in the first nostril 710 and the second stimulator unit 706 in the second nostril 712.

In some variations, the clip 702 may comprise a u-shaped portion 714 configured to receive and clamp to a portion of the nasal septum 708. This engagement between the clip 702 and the nasal septum 708 may limit advancement of the stimulator 700 into the nose (e.g., to prevent over-insertion of the stimulator 700). The clip 702 may exert sufficient pressure on the septum 708 so as to resist removal of the stimulator 700 from the nose. Accordingly, the clip 702 may allow the stimulator to be positioned in the nose of a subject, and the subject may wear the stimulator without needing to actively hold the stimulator in the nose. The clip 702 may be removed by flexing the clip 702 to disengage it from the septum. As such, the subject may be able to insert and remove the stimulator 700 him- or herself. In some variations, the clip 702 may be at least partially formed from one or more shape memory materials (e.g., a nickel-titanium alloy), such that the clip 702 may be deformed to disengage the clip 702 from the septum 708 and may return to its original shape. In some variations an exterior portion of the clip 702 may be formed from one or more insulating materials, such as described herein (e.g., PTFE, silicone, combinations thereof, or the like), and an interior portion may include an electrically conductive core (e.g., a wire of any suitable metal, such as silver, stainless steel, platinum, alloys thereof, or the like) electrically connecting the first stimulator unit 704 to the second stimulator unit 706. In these variations, the insulating outer portion of the clip 702 may prevent inadvertent electrical stimulation between the clip 702 and the subject.

Generally, each stimulator unit may comprise one or more electrodes 716. In some variations, it may be desirable for the stimulator units to comprise a radially expandable structure that may expand to contact the nasal mucosa when inserted into the nostrils. While shown in FIG. 7 as being formed from an expandable wire mesh/braid electrode, each electrode 716 may be configured in any suitable manner. For example, in some variations the electrodes may comprise a hydrogel. Additionally or alternatively, it may be desirable for the stimulator units to comprise a smooth surface to prevent tissue abrasion. The stimulator may be configured such that the electrodes 716 are placed in contact with any suitable tissue structure or structures (e.g., the nasal mucosa above the columella, such as the nasal mucosa superior to the columella (e.g., the nasal mucosa near the interface between the nasal bone and the upper lateral cartilage) when the clip 702 is connected to the nasal septum.

Generally, the first 704 and/or second 706 stimulator units may comprise a housing 720, which may comprise a control subsystem having a processor, a stimulation subsystem, and a memory. In some variations the control subsystem may have a detection subsystem. Additionally or alternatively, the stimulator may comprise a communication subsystem. The stimulator circuitry may be housed in a single housing 720 (e.g., a housing 720 of the first stimulator unit 704 or a housing 720 of the second stimulator unit), or may be divided between multiple housings (e.g., a housing 720 of the first stimulator unit 704 and a housing 720 of the second stimulator unit). In some variations, the stimulator 700 may comprise a power source (e.g., a battery) (not shown). In other variations, the stimulator 700 may be powered wirelessly (e.g., via power received from a coil 718 or other antenna).

Figure 8B:
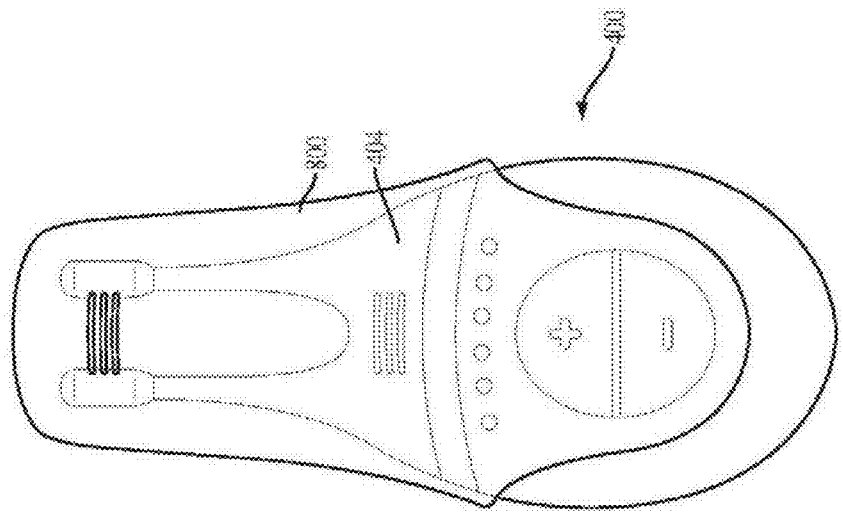
FIGS. 8A and 8B show perspective and front views, respectively, of the stimulator of FIGS. 4A-4E with an attached cap.
Figure 8A:
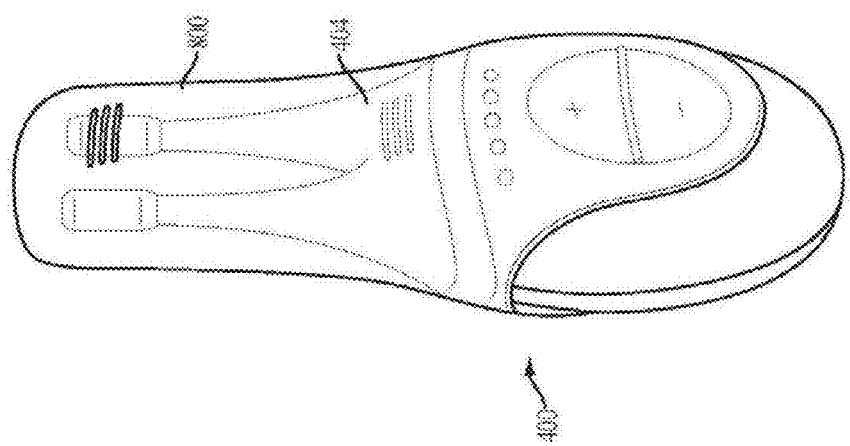

In some variations, the stimulators described here may comprise a cap to protect the stimulator probe. For example, FIGS. 8A and 8B show perspective and front views, respectively, of stimulator 400 with an attached cap 800. As shown there, the cap 800 may fit over the stimulator probe 404, which may protect the probe from contamination. More particularly, it may be desirable for the cap to protect the nasal insertion prongs, and especially the electrodes, from contamination. The systems described here may additionally or alternatively comprise a base station. The base station may be configured to releasably connect to one or more portions of the stimulator, and may be configured to perform one or more functions when connected to the stimulator. FIGS. 9A-9D depict a portion of a stimulator system comprising a base station 900 as described here. FIG. 9A shows a front view the stimulator body 902 docked in the base station 900, while FIGS. 9B, 9C, and 9D depict side, back, and top views of the base station 900, respectively. In variations where the stimulator body 902 comprises a rechargeable power source (such as a rechargeable battery, capacitor, or the like), the base station 900 may be configured to recharge the rechargeable power source.

Other variations and features of stimulator systems, devices, and their method of use suitable for employment in the methods described herein are described in U.S. patent application Ser. No. 14/256,915, filed Apr. 18, 2014, and titled "NASAL STIMULATION DEVICES AND METHODS"; in U.S. patent application Ser. No. 14/630,471, filed on Feb. 24, 2015, and titled "POLYMER FORMULATIONS FOR NASOLACRIMAL STIMULATION"; in U.S. patent application Ser. No. 14/920,860, filed Oct. 22, 2015, and titled "STIMULATION DEVICES AND METHODS FOR TREATING DRY EYE"; and in U.S. patent application Ser. No. 14/920,852, filed Oct. 22, 2015, and titled "IMPLANTABLE NASAL STIMULATOR SYSTEMS AND METHODS," each of which is hereby incorporated by reference in its entirety.

Methods

Described herein are methods for increasing mucin and other tear proteins on an ocular surface of a subject. The methods generally include intranasally delivering an electrical stimulation to the subject, e.g., to the nasal mucosa of the subject. The intranasally delivered electrical stimulation may stimulate release of one or more ocular mucins to thereby improve a condition of the eye. In some instances, the intranasally delivered electrical stimulation stimulates or increases mucin release by stimulating/triggering degranulation of goblet cells in the conjunctiva of the eye. Additionally or alternatively, the intranasally delivered electrical stimulation may help to increase tear volume on the eye, e.g., by increasing the volume of the aqueous layer. Tear meniscus height (TMH) measurements can be used assess tear volume. Additionally or alternatively, the intranasally delivered electrical stimulation may be useful in decreasing the concentration of inflammatory mediators in the tear film, or decreasing a particular type of inflammatory mediator, e.g., MMP-9 or IL-8, in the tear film.

Release of Ocular Mucins

The stimulators and methods described herein may deliver waveforms configured to stimulate release of one more ocular mucins, as further described below. In some variations, the waveforms may be pulse-based. The waveforms may be configured to stimulate tissue on both sides of the nose, or the waveforms may be configured to stimulate tissue on a single side of the nose. In other variations, the waveform may comprise symmetric biphasic pulses. The waveform may be programmed to include any suitable parameters (e.g., frequency, pulse width, amplitude) in order to enhance or trigger mucin release. In addition to the waveforms described herein, exemplary waveforms that may be used for intranasal stimulation are described in U.S. patent application Ser. No. 14/809,109, filed Jul. 24, 2015, and titled "STIMULATION PATTERNS FOR TREATING DRY EYE," which is hereby incorporated by reference in its entirety.

Electrical stimulation may be intranasally delivered for at least 5 minutes, at least 4 minutes, at least 3 minutes, at least 2 minutes, at least 1 minute, at least 30 seconds, at least 15 seconds, at least 10 seconds, or at least 5 seconds. In one variation, the electrical stimulation may be intranasally delivered for a duration of 3 minutes or at least 3 minutes. In other variations, the electrical stimulation may be intranasally delivered for a duration ranging from 30 seconds to one 1 minute, from 30 seconds to 1.5 minutes (90 seconds), from 30 seconds to 2 minutes (120 seconds), from 30 seconds to 2.5 minutes (150 seconds), or from 30 seconds to 3 minutes (180 seconds). The electrical stimulation may be repeated any number of times using the same waveform or a different waveform.

Generally, the stimulus may comprise a waveform of less than about 200 Hz. In some of these variations, the frequency is preferably between about 10 Hz and about 200 Hz.

In some of these variations, the frequency is preferably between about 30 Hz and about 150 Hz. In others of these variations, the frequency is preferably between about 50 Hz and about 80 Hz. In others of these variations, the frequency is preferably between about 30 Hz and about 60 Hz. In some variations, the frequency may be about 1.5 Hz, about 10.25 Hz, about 70 Hz, about 150 Hz, about 25 Hz, about 27.5 Hz, about 30 Hz, about 32.5 Hz, about 35 Hz, about 37.5 Hz, about 40 Hz, about 42.5 Hz, about 45 Hz, about 47.5 Hz, about 50 Hz, about 52.5 Hz, about 55 Hz, about 57.5 Hz, about 60 Hz, about 62.5 Hz, or about 65 Hz.

Generally, when the stimulus comprises a biphasic pulse and the first phase of the biphasic pulse is current-controlled, the first phase may preferably have an amplitude between about 1.0 mA and about 10 mA. Amplitudes within these ranges may be high enough to stimulate targeted tissue, but sufficiently low as to avoid any significant heating of tissue, ablation of tissue, or the like. In some variations the amplitude may be between about 1.0 mA and about 5.0 mA. In other variations, the first phase may have an amplitude of about 0.1 mA, about 0.2 mA, about 0.3 mA, about 0.4 mA, about 0.5 mA, about 0.6 mA, about 0.7 mA, about 0.8 mA, about 0.9 mA, or about 1.0 mA. In some variations, the amplitude may be variable. For example, the amplitude may vary between about 1.3 mA and about 1.5 mA, about 2.2 mA and about 2.5 mA, about 3.2 mA and about 3.7 mA, about 4.3 mA and about 5.0 mA. When the first phase of a biphasic pulse is voltage-controlled, the first phase may preferably have an amplitude between about 10 mV and about 100 V.

Figure 10A:
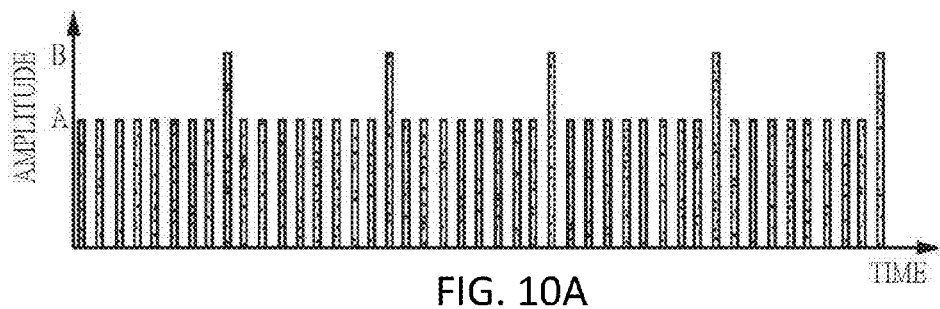
FIGS. 10A-10D illustrate exemplary amplitude modulation waveform parameters.
Figure 10B:
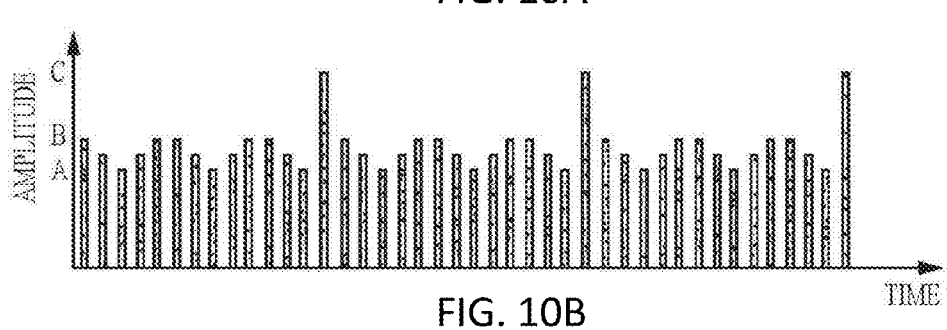
Figure 10C:
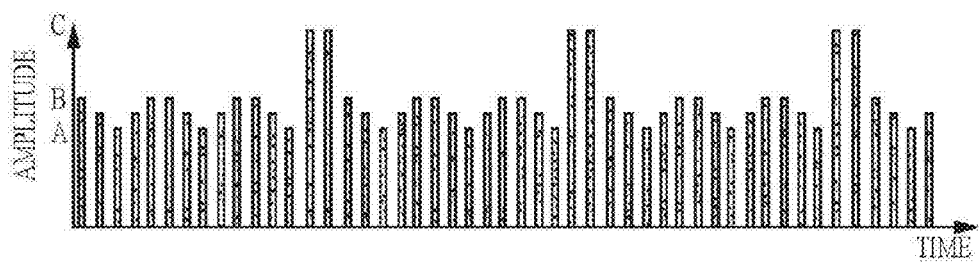
Figure 10D:
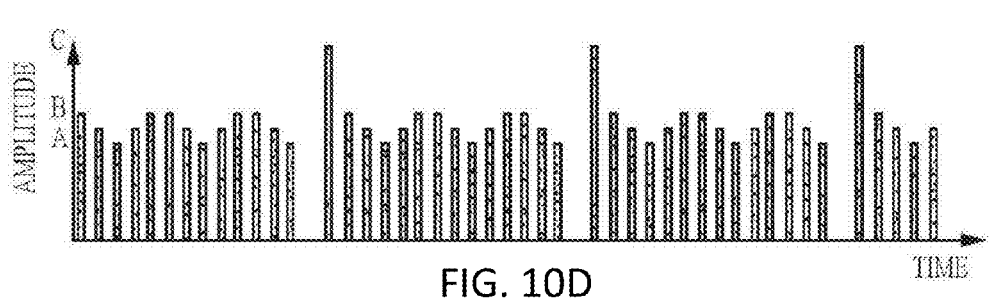

When a stimulator is configured to deliver a pulse-based waveform, in some variations, the amplitude of the pulses may be constant over time. In other variations, the amplitude of the pulses may vary over time. This may reduce subject accommodation to the stimulation. In some variations, the amplitude of pulses may increase (linearly, exponentially, etc.) from a minimum value to a maximum value, drop to the minimum value, and repeat as necessary. In some variations, the amplitude of the pulses may vary according to a sinusoidal profile. In another variation, as illustrated in FIG. 10A, the amplitude may periodically increase from a baseline amplitude (A) to a higher amplitude (B) for a single pulse. In yet another variation, as illustrated in FIGS. 10B-10C, the amplitude of the pulses may follow a periodically increasing and decreasing pattern between two lower amplitudes (A, B), and periodically increase to a higher amplitude (C) for a single pulse (FIG. 10B) or for a plurality of pulses (e.g., two pulses) (FIG. 10C). In yet another variation, as illustrated in FIG. 10D, a higher amplitude pulse (or pulses) may be preceded by a brief pause (i.e., no current delivery). Each of these types of amplitude modulation may be implemented alone or in combination with any other type of amplitude modulation, and may reduce subject accommodation.

In some variations in which the amplitude varies over time, the amplitude may vary at a frequency suitable for reducing subject accommodation or increasing subject comfort, such as between about 0.1 Hz and about 5 Hz, between about 1 Hz and about 5 Hz, between about 1 Hz and 2 Hz, between about 2 Hz and 3 Hz, between about 3 Hz and 4 Hz, or about 4 Hz and about 5 Hz. In some variation, the amplitude may vary at a frequency of about 1.0 Hz, about 1.1 Hz, about 1.2 Hz, about 1.3 Hz, about 1.4 Hz, about 1.5 Hz, about 1.6 Hz, about 1.7 Hz, about 1.8 Hz, about 1.9 Hz, about 2.0 Hz, about 2.1 Hz, about 2.2 Hz, about 2.3 Hz, about 2.4 Hz, about 2.5 Hz, about 2.6 Hz, about 2.7 Hz, about 2.8 Hz, about 2.9 Hz, about 3.0 Hz, about 3.1 Hz, about 3.2 Hz, about 3.3 Hz about 3.4 Hz, about 3.5 Hz, about 3.6 Hz, about 3.7 Hz, about 3.8 Hz, about 3.9 Hz, or about 4.0 Hz. In other variations, the stimulation waveform may be a modulated high frequency signal (e.g., sinusoidal), which may be modulated at a beat frequency of the ranges described above. In such variations, the carrier frequency may be between about 100 Hz and about 100 kHz.

When the stimulus comprises a biphasic pulse, the first phase may preferably have a pulse width between about 1 μs and about 10 ms. In some of these variations, the pulse width may be between about 10 μs and about 100 μs. In other variations, the pulse width may be between about 100 μs and about 1 ms. In yet other variations, the pulse width may be between about 0 μs and about 300 μs. In yet other variations, the pulse width may be between about 0 μs and 500 μs.

Figure 11A:
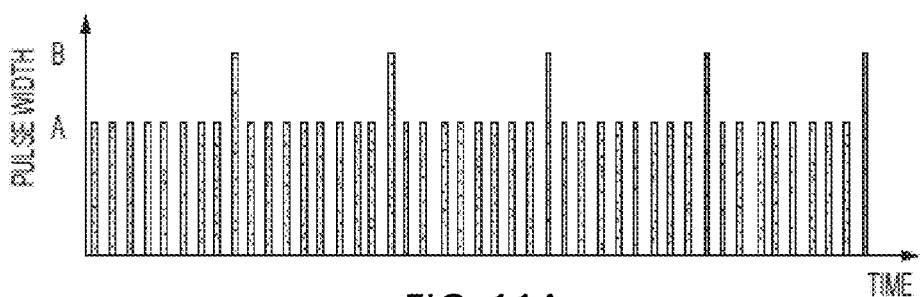
FIGS. 11A-11D and FIG. 12 illustrate exemplary pulse width modulations.
Figure 11B:
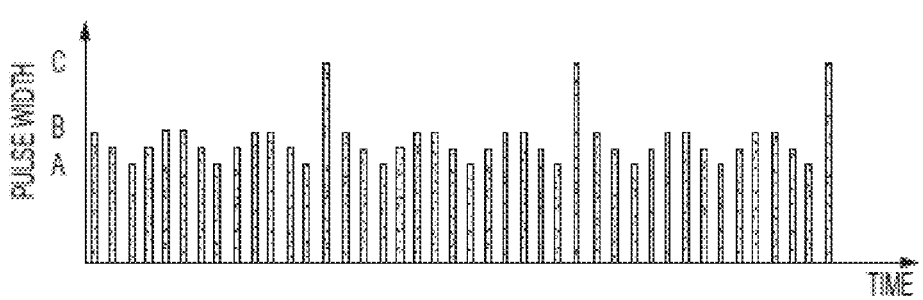
Figure 11C:
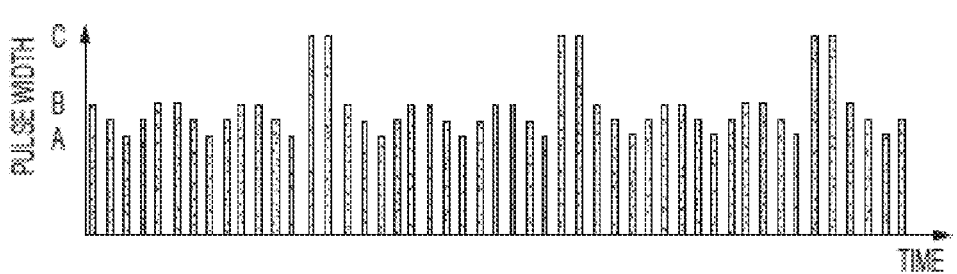
Figure 11D:
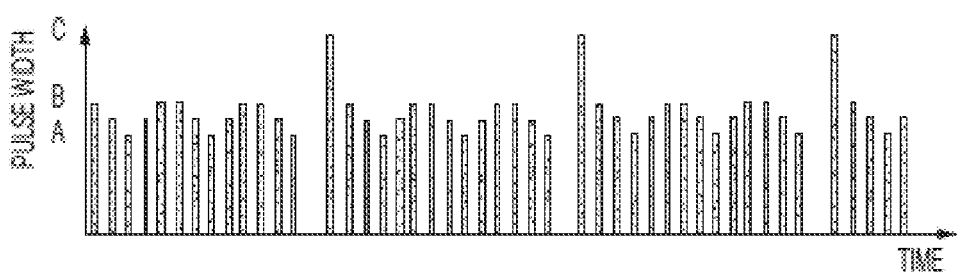

In some variations, the pulse width may be constant over time. In other variations, the pulse width may vary over time. Pulse width modulation over time may increase the efficacy and/or comfort of the stimulation. In some variations, the pulse width may increase (linearly, exponentially, etc.) from a minimum value to a maximum value, drop to the minimum value, and repeat as necessary. In some variations, the pulse width may vary according to a sinusoidal profile. In another variation, as illustrated in FIG. 11A, the pulse width may periodically increase from a baseline pulse width (A) to a longer pulse width (B) for a single pulse. In yet another variation, as illustrated in FIGS. 11B-11C, the pulse width may follow a periodically increasing and decreasing pattern between two shorter pulse widths (A, B), and periodically lengthen to a longer pulse width (C) for a single pulse (FIG. 11B) or for a plurality of pulses (e.g., two pulses) (FIG. 11C). In yet another variation, as illustrated in FIG. 11D, a longer pulse width pulse (or pulses) may be preceded by a brief pause (i.e., no current delivery). Each of these types of pulse width modulation may be implemented alone or in combination with any other type of pulse width modulation. In any form of pulse width modulation, the pulse width may vary at any suitable frequency. In some variations the pulse width may vary at about 0.1 Hz, about 0.2 Hz, about 0.3 Hz, about 0.4 Hz, about 0.5 Hz, about 0.6 Hz, about 0.7 Hz, about 0.8 Hz, about 0.9 Hz, about 1 Hz, about 1.1 Hz, about 1.2 Hz, about 1.3 Hz, about 1.4 Hz, or about 1.5 Hz. In some variations, modulation of the pulse width at a rate between about 0.5 Hz and 1 Hz may be desirable to increase subject comfort during stimulation.

In some variations, the increase and decrease of pulse width may be defined by a function implemented by the stimulator. For example, the pulse width may be defined by a function such that the pulse width varies exponentially. In one variation, the function defining pulse width may comprise two phases—a first phase during which the pulse width of the leading pulse increases over time, and a second phase during which the pulse width of the leading pulse decreases over time. During the first phase, the pulse width of the leading pulse approaches the maximum pulse width according to an exponential function, where at time t, PW{t} is defined by the equation $$PW\{t\} = (PW_{max} - PW_{min})\left(1 - e^{-\left(\frac{t}{\tau}\right)}\right)$$

where $PW_{max}$ is the maximum allowed pulse width, $PW_{min}$ is the minimum allowed pulse width, and τ is a time constant.

Once a predetermined amount of time has elapsed (a multiple of time constant τ), the pulse width modulation may enter the second phase. During the second phase, the pulse width of the leading pulse exponentially decays from its maximum value to a minimum value following the exponential equation $$PW\{t\} = (PW_{max} - PW_{min})\left(e^{-\left(\frac{t}{\tau}\right)}\right).$$

Figure 12:
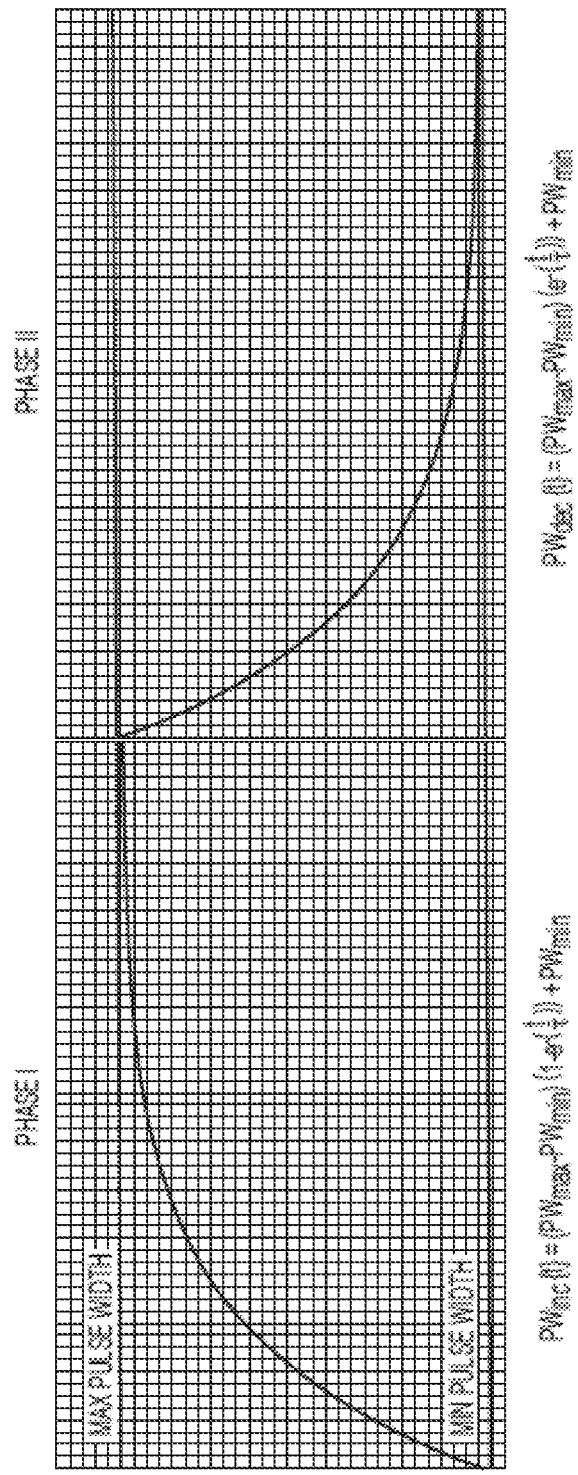

After a predetermined amount of time has elapsed (a multiple of time constant τ), the pulse width modulation may re-enter the first phase, and the cycle may repeat. The pulse width of the secondary (charge balancing) pulse is increased and decreased accordingly to retain charge full balancing. PWmax, PWmin, and τ may have any suitable values to achieve the pulse widths described herein, but in one example the waveform may have a PWmax of 300 µs, PWmin of 0 µs, and τ of ⅕ µs. In other variations, for example, PWmax, may be about 100 µs, about 200 µs, about 300 µs, about 400 µs, or about 500 µs; PWmin may be about 0 µs, about 10 µs, about 50 µs, or about 100 µs; and τ may be about ⅓ µs, about ¼ µs, about ⅕ µs, or about ⅙ µs. An exemplary function defining exponentially increasing and decaying pulse widths is shown in FIG. 12.

In some instances, the waveforms may be delivered in a continuous fashion, while in other instances, the waveforms may be delivered in a non-continuous fashion having on periods and off periods. Exemplary on/off durations include without limitation, 1 second on/1 second off, 1 second on/2 seconds off, 2 seconds on/1 seconds off, 5 seconds on/5 seconds off, 0.2 seconds on/0.8 seconds off, less than 1 second on/less than 10 seconds off. Non-continuous delivery with on and off periods may help to reduce subject accommodation and/or may be more effective than continuous delivery in causing mucin release.

Some variations of the methods described herein may comprise adjusting the waveform parameters based on feedback. In some variations the feedback may help to adjust the stimulus to be maximally effective in causing mucin release. Additionally or alternatively, the feedback may help to adjust the stimulus to prevent accommodation while limiting unpleasant sensations, such as a feeling of needing to sneeze.

The stimulators described herein may be used to intranasally deliver an electrical stimulation to increase release of one or more ocular mucins in the tear film, as previously stated. The methods may comprise intranasally delivering the stimulation to trigger goblet cell degranulation, mucin secretion from corneal, conjunctival, and/or apical cells into the tear film and/or glycocalyx. The intranasally delivered stimulation may also be used to promote sustained increases in mucin content of tears.

Ocular mucins include without limitation, MUC1, MUC2, MUC4, MUC5AC, MUC7, MUC13, MUC15, MUC16, and MUC 17. These ocular mucins may further be characterized as secreted mucins and transmembrane mucins. Exemplary secreted mucins are MUC2, MUC5AC, and MUC7. Exemplary transmembrane mucins include MUC1, MUC4, MUC13, MUC15, MUC16, and MUC17. In some variations, the intranasally delivered electrical stimulation may be used to increase release of secreted mucin MUC5AC. Referring to the Examples, the study described in Example 1 demonstrated that intranasally delivered electrical stimulation increases the release of MUC5AC by stimulating degranulation of conjunctival goblet cells. Differences between healthy (control) subjects and those with dry eye were noted by histology (not shown) from conjunctival samples obtained by impression cytology and then stained for MUC5AC and by Periodic acid-Schiff (PAS), and by a comparison of ratios of degranulated to non-degranulated cells in the samples obtained before and after sham (extranasal) stimulation and intranasal stimulation. Upon staining, non-degranulated goblet cells were typically defined by their uniform size, intact cell borders, and intracellularly packaged mucins, while degranulated goblet cells were characterized by disrupted cell borders and scattered mucin granules. In some instances, PAS and MUC5AC stained specimens revealed clusters of degranulated goblet cells after intranasal stimulation. These clusters were not observed in cytology specimens taken at baseline and after extranasal stimulation. The stimulator used for such stimulation was similar to the device described in FIGS. 4A-4E and FIG. 5.

Specifically, the results obtained from MUC5AC staining indicated that the ratio of degranulated to non-degranulated goblet cell densities from subjects with dry eye was significantly higher after intranasal stimulation (4.71±4.48) compared to those taken at baseline (0.74±0.62, $p<0.001$) and after sham stimulation (0.57±0.54, $p<0.001$). See Table 1 in Example 1 for a complete listing of results after stimulation. PAS staining also demonstrated a significant increase in the ratio of degranulated to non-degranulated goblet cell densities after the delivery of intranasal stimulation in dry eye subjects (2.02±1.41) compared to those taken at baseline (0.73±0.36, $p=0.001$) and after sham stimulation (0.69±0.39, $p=0.001$). See Table 4 in Example 1 for a complete listing of results after stimulation.

Additional results obtained from inferior bulbar (IB) conjunctiva and temporal bulbar (TB) conjunctiva cytology specimens taken from all study participants and stained for MUC5AC revealed a significantly higher ratio of degranulated to non-degranulated goblet cells after intranasal stimulation (IB: 2.28±1.27 and TB: 1.81±1.01) compared to baseline (IB: 0.56±0.55, $p=0.015$) (TB: 0.56±0.32, $p=0.003$) and extranasal sham application (IB: 0.37±0.29, $p=0.001$) (TB: 0.39±0.33, $p=0.001$). When the same analysis was repeated in the dry eye or control groups, the ratio was significantly higher after intranasal stimulation than the baseline ratio and ratio after extranasal application in both groups ($p<0.05$). Moreover, while control subjects had a higher ratio of degranulated to non-degranulated goblet cells at baseline (0.75±0.52) compared to the dry eye group (0.41±0.27), the ratio became slightly higher in dry eye (2.04±1.12 vs. 1.99±1.21 in control) after intranasal stimulation application. A significant increase in the mean degranulated goblet cell density was also observed after intranasal stimulation. There was no significant difference between the IB or TB conjunctiva locations in terms of the effectiveness of the intranasal stimulation application on conjunctival goblet cell secretory response.

Data obtained from a single center, single-arm, study that included 15 dry eye subjects (22 eyes) specifically relating to morphological goblet cell changes before and after three minutes of intranasal stimulation showed a significant reduction in goblet cell area and perimeter. These results are provided in Example 4. Other image data that was obtained (not shown) before and after stimulation demonstrated that ocular goblet cells are smaller post nasal stimulation, indicating that ocular mucins are being released from the conjunctiva right on the eye and not just the conjunctiva of the eye lid.

Figure 23:
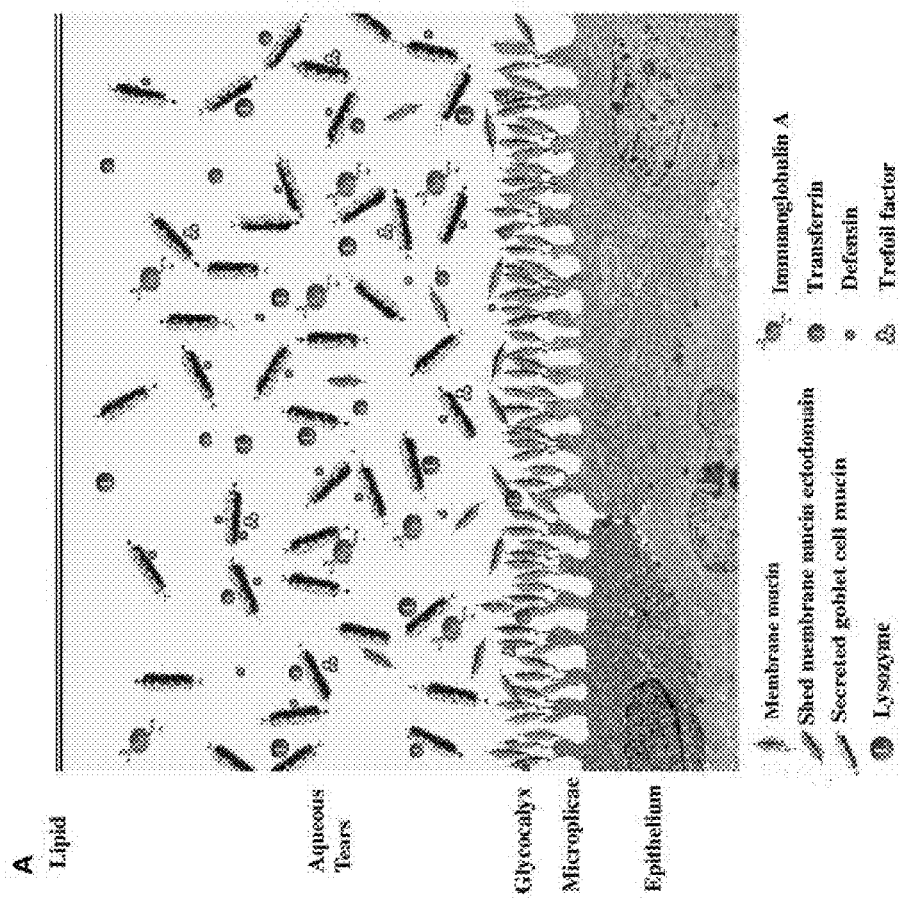
FIG. 23 is a schematic diagram of how ocular mucins function together with the glycocalyx to reduce inflammation on the eye surface.

In some variations, the intranasally delivered electrical stimulation may be used to increase release of a transmembrane mucin. For example, the intranasally delivered electrical stimulation may be used to increase release of MUC1, MUC4, MUC13, MUC15, MUC16, MUC17, or combinations thereof. Referring to FIG. 23, these membrane-associated mucins form a dense barrier in the glycocalyx at the epithelial tear film interface. In turn, this barrier prevents pathogen penetrance and is a lubricating surface that allows lid epithelia to glide over the corneal epithelia without adherence. The secreted mucins generally move easily over the glycocalyx mucins because both have anionic character that creates repulsive forces between them. In other variations, the intranasally delivered electrical stimulation may be used to increase release of an ocular mucin from acinar cells of the lacrimal gland or apical cells of the conjunctiva and cornea.

In general, the ocular glycocalyx in combination with other mucins provides a covering over the ocular surface, and helps to shield the ocular surface from bacteria, dust, and allergens, as previously stated. Given that intranasal stimulation may stimulate release of mucin from goblet cells, and may stimulate release of proteins in the lacrimal tears, a complete glycocalyx may be formed that may be beneficial to the healing process of corneal/conjunctival tissue. With a complete glycocalyx, symptoms due to allergy and/or eye dryness may be reduced. Mucin further functions as lubricant and/or cushion between the ocular surface and the eye lids that helps protect against scratching of the ocular surface. Accordingly, in some variations, increasing mucin release via intranasal stimulation may be performed as desired to help extend the comfortable wear time for contact lenses.

The stimulation may be delivered to the nasal mucosa. In some instances, the targeted area may comprise tissue innervated by the anterior ethmoidal branch of the nasociliary nerve. In some instances, the targeted area may comprise tissue innervated by the nasopalatine nerve. In some instances, the targeted area of the nasal mucosa may be superior to the columella. It may in some instances be near the inferior end of the nasal bone (i.e., near the interface between the nasal bone and the upper lateral cartilage). As such, the stimulus may be delivered between about 20 mm and about 35 mm into the nasal cavity of the patient, in some cases via an electrode between about 25 mm and about 35 mm into the nasal cavity of the patient. In other instances, the targeted area may be the columella. It may be desirable that the stimulus be delivered in the anterior portion of the nasal cavity, within the nostrils and anterior to the turbinates, and in some instances, at a location anterior to the middle turbinate, or at a location anterior to the inferior turbinate. The stimulus may be delivered at least partially through tissue of or near the septum, and it may in some instances be desirable to direct the stimulus such that a portion is directed toward the front of the nose. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth, and which may reduce rhinorrhea. It may also in some instances be desirable to direct the stimulus so as to reduce negative side effects that may occur from stimulation of the olfactory area.

The methods described herein may comprise intranasally delivering stimulation according to one or more treatment regimens. For example, to increase mucin release, stimulation may be delivered to a subject as needed and/or according to a predetermined plan. In some variations, it may be desirable that each round of stimulation is long enough to result in acute mucin secretion. Intranasal stimulation may be employed for about 30 seconds to about 1 minute to achieve mucin release. At 30 seconds of stimulation, some mucin release may be obtained while at 1 minute, the release of mucin may be more robust due to, e.g., the longer stimulation triggering a larger number of goblet cells to degranulate or the longer stimulation allowing more mucin to be released from goblet cells. It may in some instances take several or more minutes of intranasal stimulation to achieve mucin release. For example, in a patient with severe dry eye, it may take about 5 to 10 minutes to achieve mucin release, while in a patient with moderate dry eye, it may take about 3 to 5 minutes to achieve mucin release, while in a patient without dry eye, it may take only about 1 minute to achieve mucin release with particular stimulus parameters. In some variations, the methods described herein may comprise an initial round of stimulation that is longer than subsequent rounds of stimulation. The initial round of stimulation may in some variations be of a length sufficient to achieve mucin release in a patient with dry eye who has not previously been treated with electrical intranasal stimulation.

The initial round of stimulation may in some methods be performed under the supervision of a medical professional, while subsequent rounds of stimulation may be performed without supervision of a medical professional (e.g., at home). In some variations, the initial and subsequent rounds of stimulation may be delivered using different stimulators. These stimulators may be configured with different waveforms, and/or may have different physical configurations. For example, the initial round of stimulation may be delivered using a stimulator configured for hands-free use (e.g., may comprise nasal insertion prongs biased toward each other and/or a strap to hold the nasal insertion prongs in a subject's nose), while subsequent rounds of stimulation may be delivered using a stimulator not configured for hands-free use (e.g., a stimulator not comprising a strap and having parallel nasal insertion prongs). As another example, a stimulator used under supervision of a medical professional (e.g., for the initial round of stimulation) may be fully disposable, while a stimulator used without such supervision (e.g., for subsequent stimulation rounds) may be at least partially reusable.

In some variations, the intranasally delivered electrical stimulation may help to increase tear volume on the eye, e.g., by increasing the volume of the aqueous layer. Tear meniscus height (TMH) measurements can be used assess tear volume. For example, and as provided in Example 2 and FIG. 20, TMH measurements taken before and after the intranasal delivery of electrical stimulation demonstrated a statistically significant increase after intranasal application in both dry eye and control groups (p value equal to about 0.04 for both). In one dry eye subject with Sjögren's syndrome, intranasal stimulation increased tear meniscus height in the right eye by about 135% (95 µm to 225 µm) and in the left eye by about 82% (130 µm to 237 µm). Other findings in normal subjects demonstrated a significant correlation between TMH change and the degranulated to non-degranulated goblet cell ratio in MUC5AC stained cytology specimens; however, no significant correlation was found in dry eye patients. Overall, the impression cytology and TMH data demonstrate that intranasal stimulation triggers conjunctival goblet cell mucin secretion, and can provide a new approach to treatment of dry eye because it can stimulate aqueous tear production by the lacrimal glands as well as mucin secretion by goblet cells.

Figure 21:
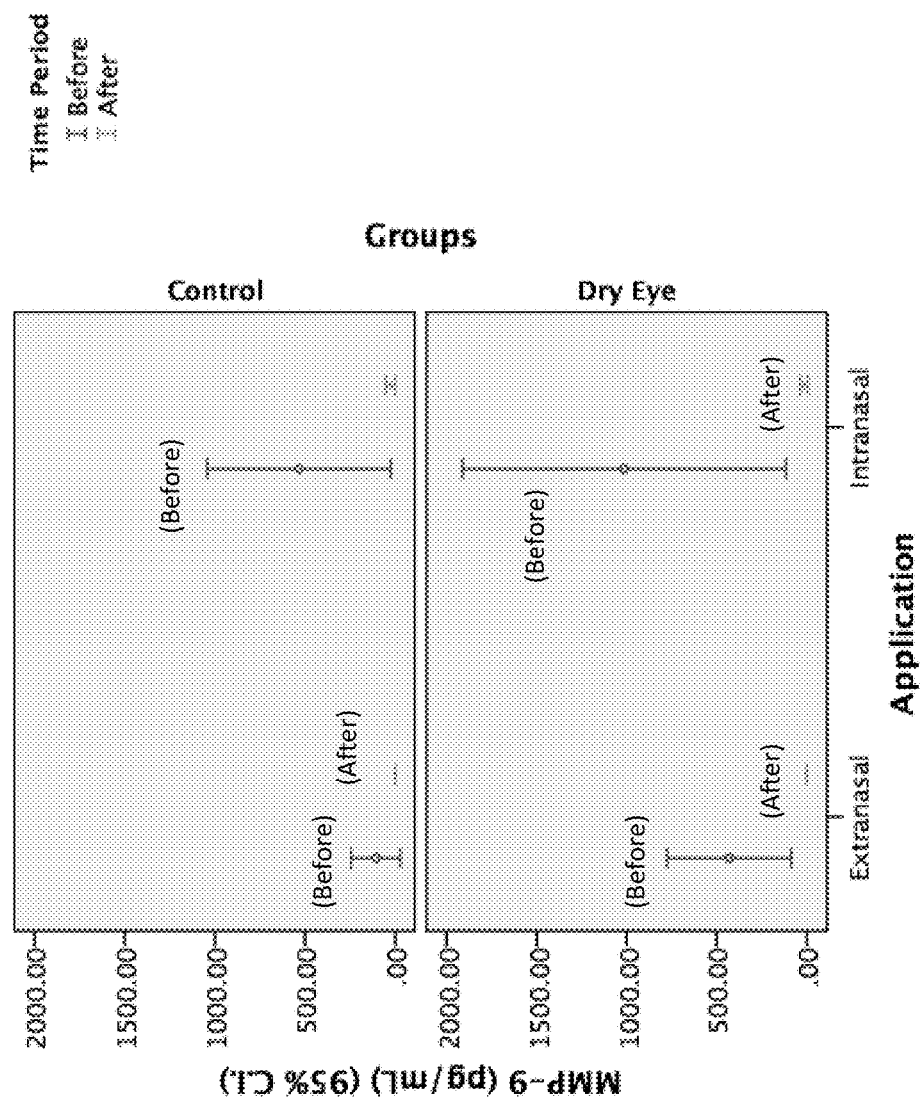
FIG. 21 is a graph of the data provided in Table 7 relating to decreases in MMP-9 concentrations in the tear fluid of control and dry eye subjects before and after application of extranasal and intranasal stimulation.
Figure 22:
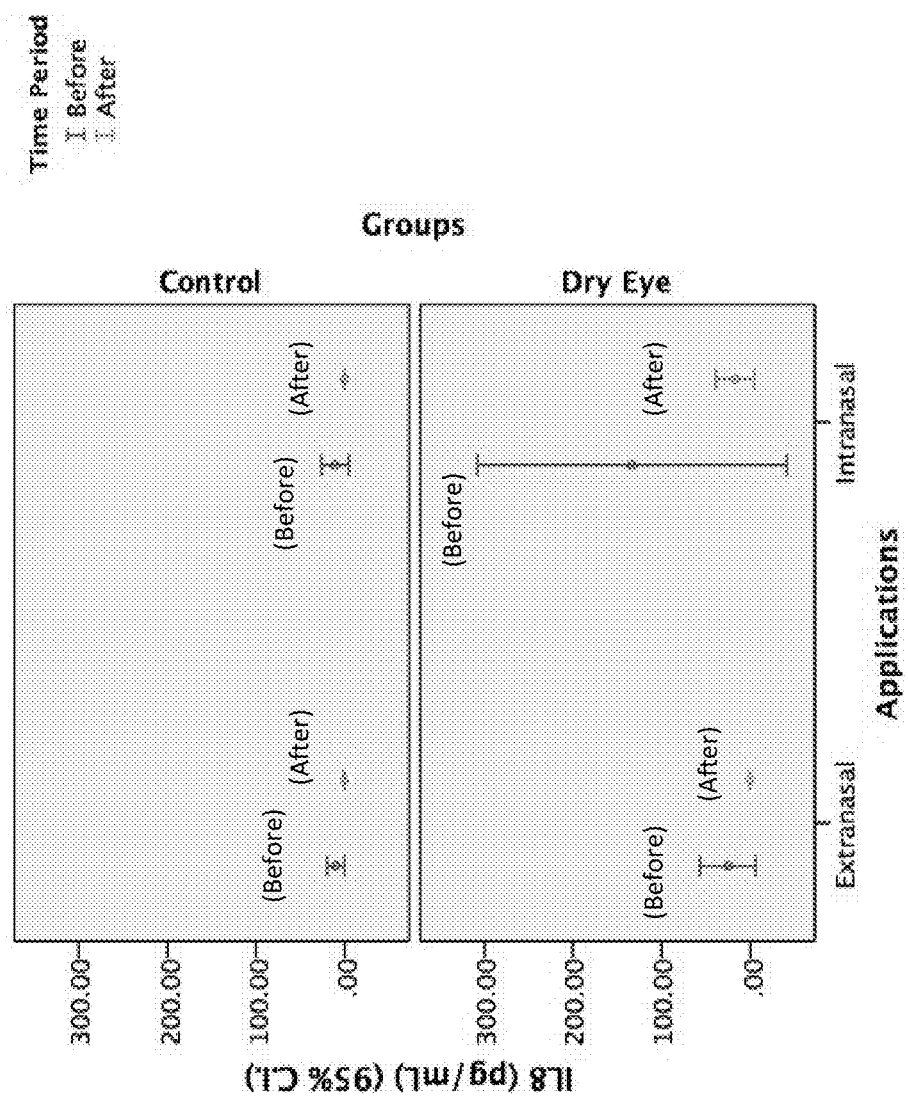
FIG. 22 is a graph illustrating the decrease in IL-8 concentrations in the tear fluid of control and dry eye subjects before and after application of extranasal and intranasal stimulation.

Additionally or alternatively, the intranasally delivered electrical stimulation may be useful in decreasing the concentration of inflammatory mediators in the tear film, or decreasing a particular type of inflammatory mediator, e.g., MMP-9 or IL-8, in the tear film. For example, as provided in Example 3 and FIG. 21, there was a decrease in MMP-9 concentration in the tear samples after the intranasal application of stimulation, which appeared to more be prominent in the dry eye group (decrease from 3372.37 pg/mL to 0.6 pg/mL). Data illustrating the decrease in IL-8 concentration as compared to controls after intranasal stimulation application is provided in Example 3 and FIG. 22.

The intranasally delivered electrical stimulation may be used to improve or treat various ocular surface diseases or various conditions of the eye. For example, the intranasal stimulation may be used to improve dry eye or ocular inflammation. In one variation, the intranasal stimulation may be used to improve dry eye or ocular inflammation associated with Sjögren's syndrome. In other variations, the condition of the eye is an unstable tear film or an unstable glycocalyx. Intranasal stimulation to increase mucin release for these conditions may optionally be used in conjunction with other therapies. In some variations, the intranasally delivered electrical stimulation is used in conjunction with one or more punctum plugs. In other variations, the intranasal stimulation may be administered in conjunction with application of one or more active agents, e.g., cyclosporine or lifitegrast, to the ocular surface. The one or more active agents may comprise one or more antibacterial agents, one or more anti-inflammatory agents, one or more antihistamines, one or more immunomodulators, one or more immunohistomodulators, or combinations thereof. Patients receiving intranasal stimulation may also be treated with topical treatments (e.g., artificial lubricants (e.g., lipid-based artificial tears), topical steroids, topical cyclosporine, topical lifitegrast, topical azithromycin, topical antibiotics (e.g., bacitracin)), topical antihistamines, oral antihistamines, oral antibiotics (e.g., oral tetracycline, oral doxycycline), nutritional supplements (e.g., fish oil, gamma-linolenic acid), and combinations thereof. In some variations, the intranasally delivered electrical stimulation is delivered in response to symptomatic need. In other variations, the intranasally delivered electrical stimulation is delivered to avoid a symptomatic need.

Studies conducted by the inventors thus far have captured the release of MUC5AC as the predominant mucin in the eye. However, there are other ocular mucins, as noted herein, and these mucins have different functions. Some function more as glue to keep the tears up longer (increasing tear film stability and tear film breakup time), while others encapsulate dust, allergens, bacteria etc. By encapsulating these "intruders," mucins function together with the "glycocalyx" (FIG. 23) to prevent the intruders from directly contacting the corneal & conjunctival surface, which reduces the sensory input that would drive an inflammatory and/or histamine response. This in turn may decrease redness of the eyes, and decrease the concentration of inflammatory mediators on the eye surface. Accordingly, in some variations, intranasally delivered electrical stimulation may be used in combination with Restasis® Ophthalmic Emulsion ("Restasis") (Allergan, Parsippany, N.J.) in the treatment of dry eye. To further explain, treatment first with Restasis may help to increase goblet cell density by reducing ocular surface inflammation. These goblet cells (as well those in the lacrimal gland) can then be triggered to release mucin. In this manner, treatment with Restasis and intranasal stimulation may be synergistic. This combined treatment may be beneficial in those individuals with severe dry eye and high levels of ocular inflammation.

Release of Other Tear Proteins

In patients with dye eye, the proper amount of tear proteins in the aqueous layer of the tear film may be lacking, in addition to, or alternatively to, mucin. The abnormal tear protein production may be due to systemic diseases (e.g., Sjögren's syndrome), medications, or other causes. In some variations, the methods described herein may use the application of intranasal stimulation, in the same manner as described for mucin, to increase other tear protein release into the tear film, e.g., the aqueous layer of the tear film.

Accordingly, methods for increasing secretion of tear proteins other than mucin on the ocular surface by intranasally delivering electrical stimulation to a subject are also described herein. For example, secretion of tear proteins such as lysozyme, lactoferrin, tear specific prealbumin, caeruloplasmin, lacitin, lipophilin, immunoglobulins such as IgA, IgD, IgE, and IgG, or combinations thereof, can be triggered by intranasally delivering electrical stimulation. The intranasal stimulation may be delivered for at least 5 minutes, at least 4 minutes, at least 3 minutes, at least 2 minutes, at least 1 minute, at least 30 seconds, at least 15 seconds, at least 10 seconds, or at least 5 seconds. In some instances, the electrical stimulation may be intranasally delivered for a duration of 3 minutes or at least 3 minutes. In other instances, the electrical stimulation may be intranasally delivered for a duration ranging from 30 seconds to one 1 minute, from 30 seconds to 1.5 minutes (90 seconds), from 30 seconds to 2 minutes (120 seconds), from 30 seconds to 2.5 minutes (150 seconds), or from 30 seconds to 3 minutes (180 seconds). Some variations of the method may include delivering intranasal stimulation to a subject for about 3 minutes to increase lysozyme and/or lactoferrin secretion into the tear fluid and onto the ocular surface. Referring to Example 5, data illustrating the increase in lysozyme and lactoferrin concentrations as compared to controls after intranasal stimulation application is provided. The electrical stimulation may be repeated any number of times using the same waveform or a different waveform.

Optimizing Intranasal Delivery of Electrical Stimulation

In general, aqueous tear production is readily sensed by a subject. However, the subject may not be able to identify when tear components such as mucin or other tear proteins are released. Accordingly, in addition to the intranasal delivery of electrical stimulation, the methods may comprise obtaining feedback relating to the efficacy of the delivered electrical stimulation by measuring impedance or an electromyogram (EMG) signal. Impedance may reflect the efficacy of the delivered electrical stimulation by indicating that sufficient current is able to flow from the stimulator into tissue. An EMG signal may reflect the efficacy of the delivered electrical stimulation because in some instances, neural stimulation of the anterior ethmoidal nerve may trigger muscle contractions of the orbicularis oculi and muscles on the cheek and of the nose as the patient controls an urge to sneeze. As such, EMG signals measured from facial muscles of the nose, cheeks and around the eyes (e.g., the orbicularis oculi) may provide feedback relating to the efficacy with respect to mucin and/or other tear protein secretion.

These forms of feedback, such as impedance or an EMG signal may be used, for example, to confirm that a stimulus is being effectively delivered for the intended stimulation duration. For example, this feedback may be used to confirm that the stimulus is being effectively delivered at the beginning of a round of stimulation and/or at one or more time points during the round of stimulation. When a round of stimulation has a particular length (e.g., at least about 30 seconds of stimulation), these forms of feedback may be used to confirm that the full duration of effective stimulation is delivered. As described herein, intranasal stimulation may be employed for about 30 seconds to about 1 minute to achieve mucin release. At 30 seconds of stimulation, some mucin release may be obtained while at 1 minute, the release of mucin may be more robust due to, e.g., the longer stimulation triggering a larger number of goblet cells to degranulate or the longer stimulation allowing more mucin to be released from goblet cells. As such, it may be desirable to confirm that stimulation is effectively delivered for the full desired duration.

The impedance and/or EMG signal may be measured using the same device that delivers the electrical stimulation. For example, the stimulators described herein may be configured to measure impedance and/or an EMG at or near the stimulus delivery electrodes. In other instances, the impedance and/or EMG signal may be measured using a separate device (i.e., not the same device as the device that delivers the electrical stimulation). For example, the impedance and/or EMG signal may be measured by a separate intranasal or extranasal device. In some variations, the extranasal device may comprise a nose strip comprising detection electrodes placed on the outside of the nose.

The methods for increasing mucin and other tear proteins on the ocular surface may further include identifying an optimal stimulation location for intranasally delivering the electrical stimulation. Finding the optimal stimulation location can be accomplished by guidance or training by the physician, as further described below. Techniques for identifying the optimal stimulation location can include impedance monitoring. Additionally or alternatively, the optimal stimulation location can be identified by obtaining feedback from an electromyogram (EMG) signal from a facial muscle near the nose, cheeks, or around the eyes (e.g., the orbicularis oculi). The impedance and EMG signals can be measured intranasally using the same device that delivers the electrical stimulation. In other instances, the impedance and EMG signals can be measured by an extranasal device. In some variations, the extranasal device comprises a nose strip.

The delivery of intranasal stimulation can also be accomplished via a treatment plan that optimizes one or more stimulation parameters, e.g., duration of stimulation, frequency of the stimulation waveform, and amplitude of the stimulation waveform, and/or finds the optimal location to stimulate in order to effect the desired response. As further described herein, the treatment plan may be formulated under guidance or training by a physician. One or more parameters of the electrical stimulation waveforms may be tailored or optimized to achieve release of mucin and other tear proteins from secretory vesicles of the lacrimal gland. The one or more optimized parameters can be selected from the group consisting of duration of stimulation, type of stimulation waveform, frequency of the stimulation waveform, amplitude of the stimulation waveform, pulse width of the stimulation waveform, and combinations thereof. In some variations, the one or more optimized parameters is duration of stimulation. It may be useful for the duration of stimulation to range from about 30 seconds to about 3 minutes, or from about 30 seconds to about 1 minute. Additionally or alternatively, the one or more optimized parameters is amplitude of the stimulation waveform.

Methods for treating dry eye are also described herein. The methods generally include intranasally delivering electrical stimulation to a subject afflicted with dry eye; obtaining feedback relating to the efficacy of the delivered electrical stimulation by measuring impedance or an electromyogram (EMG) signal from a facial muscle near the nose, cheeks, or around the eyes of the subject; formulating a treatment plan based on the feedback; and continuing intranasal delivery of the electrical stimulation according to the treatment plan, where the delivered electrical stimulation increases the release of a tear protein to treat the dry eye of the subject. Exemplary tear proteins include without limitation, mucin, lysozyme, lactoferrin, tear specific prealbumin, caeruloplasmin, lacitin, lipophilin, and immunoglobulins A, D, G, and E, and combinations thereof. The methods for treating dry eye can further include identifying an optimal stimulation location for intranasally delivering the electrical stimulation. Finding the optimal stimulation location can be accomplished by guidance or training by the physician, as further described below. Techniques for identifying the optimal stimulation location can include impedance monitoring. Additionally or alternatively, the optimal stimulation location can be identified by obtaining feedback from an electromyogram (EMG) signal from a facial muscle near the nose, cheeks, or around the eyes (e.g., the orbicularis oculi). The impedance and EMG signals can be measured intranasally using the same device that delivers the electrical stimulation. In other instances, the impedance and EMG signals can be measured by an extranasal device. In some variations, the extranasal device comprises a nose strip.

The delivery of intranasal stimulation can also be accomplished via a treatment plan that optimizes one or more stimulation parameters, e.g., duration of stimulation, frequency of the stimulation waveform, and amplitude of the stimulation waveform, and/or finds the optimal location to stimulate in order to effect the desired response. As further described herein, the treatment plan may be formulated under guidance or training by a physician. One or more parameters of the electrical stimulation waveforms may be tailored or optimized to achieve release of mucin and other tear proteins from secretory vesicles of the lacrimal gland. The one or more optimized parameters can be selected from the group consisting of duration of stimulation, type of stimulation waveform, frequency of the stimulation waveform, amplitude of the stimulation waveform, pulse width of the stimulation waveform, and combinations thereof. In some variations, the one or more optimized parameters is duration of stimulation. It may be useful for the duration of stimulation to range from about 30 seconds to about 3 minutes, or from about 30 seconds to about 1 minute. Additionally or alternatively, the one or more optimized parameters is amplitude of the stimulation waveform.

Other methods for treating dry eye may include determining whether a subject afflicted with dry eye is deficient in a tear protein on an ocular surface, and based on the tear protein found to be deficient, intranasally delivering an electrical stimulation to the subject, where one or more parameters of the intranasally delivered electrical stimulation is selected based upon the deficient tear protein, and where the intranasally delivered electrical stimulation is effective to increase release or the concentration of the deficient tear protein on the ocular surface. Exemplary tear proteins include without limitation, mucin, lysozyme, lactoferrin, tear specific prealbumin, caeruloplasmin, lacitin, lipophilin, and immunoglobulins A, D, G, and E, and combinations thereof.

In some instances, the methods may include determining a type of dry eye in a subject and intranasally delivering to the subject an electrical stimulation according to a treatment plan based on the determined type of dry eye, e.g., mild dry eye, moderate dry eye, or severe dry eye. Guidance and training may be offered by the physician so that the subject learns how to properly use the stimulator device according to their treatment plan.

EXAMPLES

Examples 1-3 below relate to a three-visit study consisting of one screening opthalmological examination and two separate treatment visits for a total of 15 participants (10 with dry eye, and 5 normal). In one treatment visit, the participants were subjected to extranasal (sham) stimulation, and in the other visit, to intranasal stimulation. The types of stimulation were performed in randomized order.

Figure 13A:
FIG. 13A shows an exemplary handheld stimulator inserted into a subject's nose.
Figure 13B:
FIG. 13B shows the handheld stimulator positioned on the exterior of a subject's nose.

Stimulation was performed for three minutes using a handheld stimulation device as described in FIGS. 4A-4E. For intranasal stimulation, participants were instructed to place the tips of the handheld stimulator into both nostrils simultaneously, and toward the top and front of the nose, as shown in FIG. 13A. The participants were instructed to place the tips of the handheld stimulator on the lower part of the nose (one tip on each side) for extranasal stimulation, as shown in FIG. 13B. At the end of the second and third visits, impression cytology (IC) was performed. IC refers to the application of cellulose acetate filter to the ocular surface to remove superficial layers of the ocular surface epithelium. Cells removed in this manner can then be subjected to histological, immunological, or molecular analysis. In this study, IC was performed on the bulbar conjunctiva of the right eye for PAS (Periodic acid-Schiff) staining and from the left eye for MUC5AC mucin immunostaining.

Results from the IC relating to the degranulation of goblet cells are described in Example 1. Furthermore, tear meniscus height measurements and tear fluid samples were collected before and after each stimulation, as described in Examples 2 and 3.

Example 1: Goblet Cell Degranulation

After staining, five images from each membrane were captured at ×20 magnification with a fluorescence microscope. In these images, the ratio of degranulated to non-degranulated GC densities (GCDs) was measured as a marker of mucin release/secretion. While non-degranulated GCs were typically well defined by their uniform size, intact cell borders, and intracellularly packaged mucins, degranulated GCs were characterized by disrupted cell borders and scattered mucin granules.

The goblet cell density data was analyzed using SPSS 20.0 for Mac (SPSS Inc., Chicago, Ill., USA). Prior to statistical analysis, data distribution was checked for normality. Because of the sample size, non-parametric tests were preferred in the analysis. The Mann-Whitney U test was used to compare differences between two independent groups. The Wilcoxon signed-rank test was used when comparing repeated measurements. A p-value of less than 0.05 was considered as statistically significant.

Figure 14:
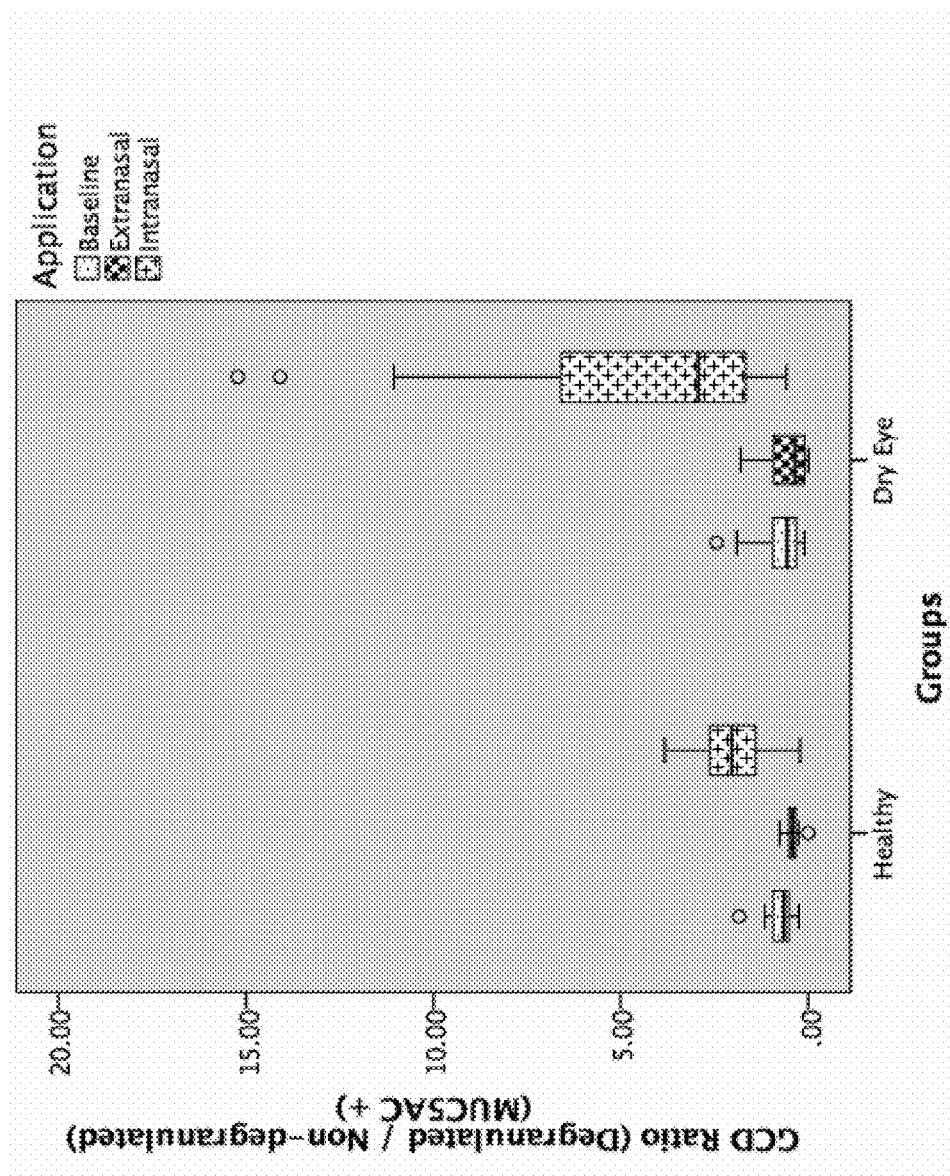
FIG. 14 is a graph of the data provided in Table 1 relating to goblet cell density (GCD) ratio (degranulated/non-degranulated) in the conjunctiva of dry eye and healthy subjects stained with MUC5AC.

The results obtained from MUC5AC staining indicated that intranasal stimulation significantly increased the degranulated to non-degranulated goblet cell density ratio in the conjunctiva of subjects with dry eye as compared to normal/healthy subjects. The degranulated to non-degranulated goblet cell density ratio data is provided below in Table 1, and graphically represented in FIG. 14. Extranasal stimulation did not significantly increase degranulated to non-degranulated goblet cell density ratios for both groups. Specifically, the results obtained from MUC5AC staining indicated that the ratio of degranulated to non-degranulated goblet cell densities from subjects with dry eye was significantly higher after intranasal stimulation (4.71±4.48) compared to those taken at baseline (0.74±0.62, p<0.001) and after sham (extranasal) stimulation (0.57±0.54, p<0.001).

TABLE 1

| Groups | A Baseline | B Extranasal Application | C Intranasal Application | P Values A-B | A-C | B-C |
|---|---|---|---|---|---|---|
| Dry Eye (n: 20) | 0.74 ± 0.62 | 0.57 ± 0.54 | 4.71 ± 4.48 | 0.333 | <0.001 | <0.001 |
| Control (n: 10) | 0.75 ± 0.52 | 0.40 ± 0.22 | 1.99 ± 1.21 | 0.082 | 0.034 | 0.001 |

Figure 15:
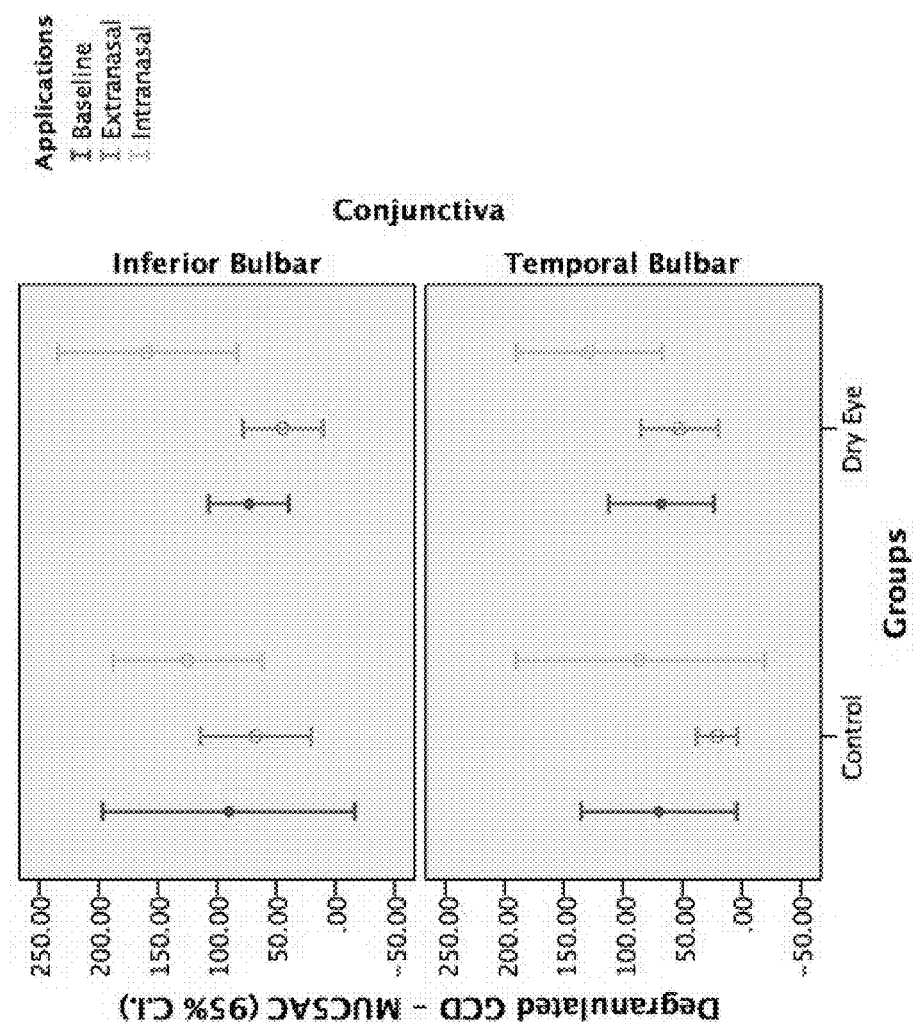
FIG. 15 is a graph of the data provided in Table 2 relating to degranulated goblet cell densities in the inferior and temporal bulbar conjunctiva stained with MUC5AC in control and dry eye subjects.

Data obtained from the MUC5AC staining also demonstrated that goblet cell degranulation occurred in various areas of the conjunctiva on the eye (bulbar conjunctiva). IC samples taken from the inferior bulbar conjunctiva (IB) and temporal bulbar conjunctiva (TB) of subjects with dry eye and normal/healthy subjects showed an increase in degranulated goblet cell densities, as provided below in Table 2, and graphically represented in FIG. 15.

TABLE 2

| Groups | Conjunc- tiva | Baseline | Extranasal Application | Intranasal Application |
|---|---|---|---|---|
| Dry Eye | IB (n: 10) | 75.11 ± 53.57 | 44.39 ± 40.79 | 175.25 ± 112.22 |
| | TB (n: 10) | 67.79 ± 62.11 | 52.28 ± 45.62 | 128.52 ± 86.01 |
| | Combined (n: 20) | 71.04 ± 56.91 | 48.77 ± 42.46 | 149.29 ± 98.35 |
| Control | IB (n: 5) | 99.06 + 96.28 | 67.23 + 29.45 | 124.87 + 39.56 |
| | TB (n: 5) | 69.73 ± 52.78 | 20.66 ± 13.69 | 85.76 ± 84.32 |
| | Combined (n: 10) | 82.77 ± 71.47 | 41.36 ± 31.96 | 103.15 ± 67.58 |

IB: Inferior bulbar
TB: Temporal bulbar

Figure 16:
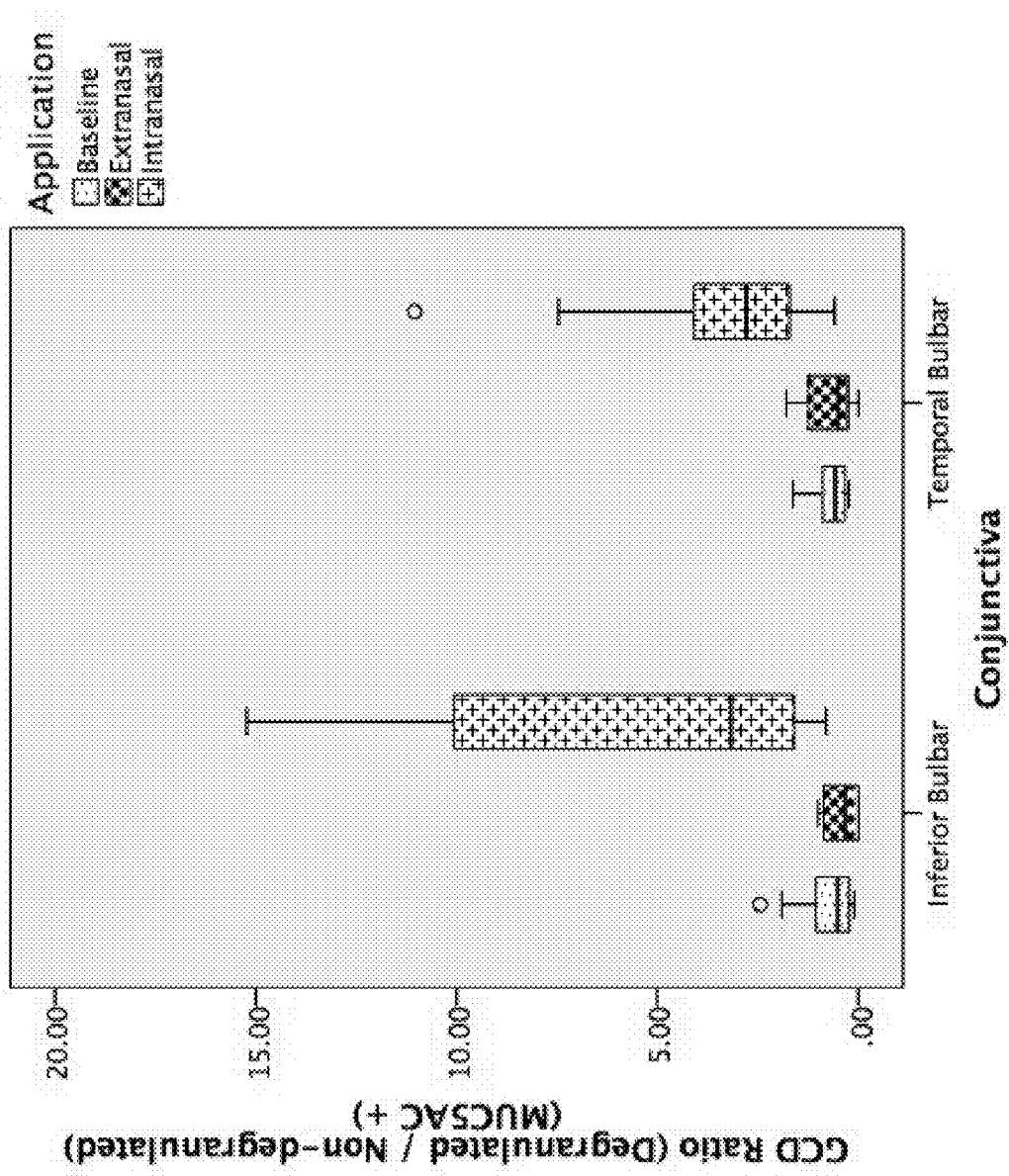
FIG. 16 is a graph of the data provided in Table 3 relating to goblet cell density (GCD) ratio (degranulated/non-degranulated) in the inferior and temporal bulbar conjunctiva of dry eye patients stained with MUC5AC.

Additionally, among dry eye participants, data obtained from the MUC5AC staining of IB and TB revealed a significantly higher ratio of degranulated to non-degranulated GCDs after intranasal stimulation compared to baseline and extranasal (sham) stimulation application (Table 3 and FIG. 16).

TABLE 3

| Conjunctiva | A- Baseline | B- Extranasal Application | C- Intranasal Application | P Values A-B | A-C | B-C |
|---|---|---|---|---|---|---|
| Dry Eye - IB (n: 10) | 0.83 ± 0.79 | 0.41 ± 0.41 | 5.68 ± 5.48 | 0.142 | 0.014 | 0.012 |
| Dry Eye - TB (n: 10) | 0.66 ± 0.42 | 0.73 ± 0.61 | 3.73 ± 3.21 | 0.728 | 0.012 | 0.009 |

Figure 17:
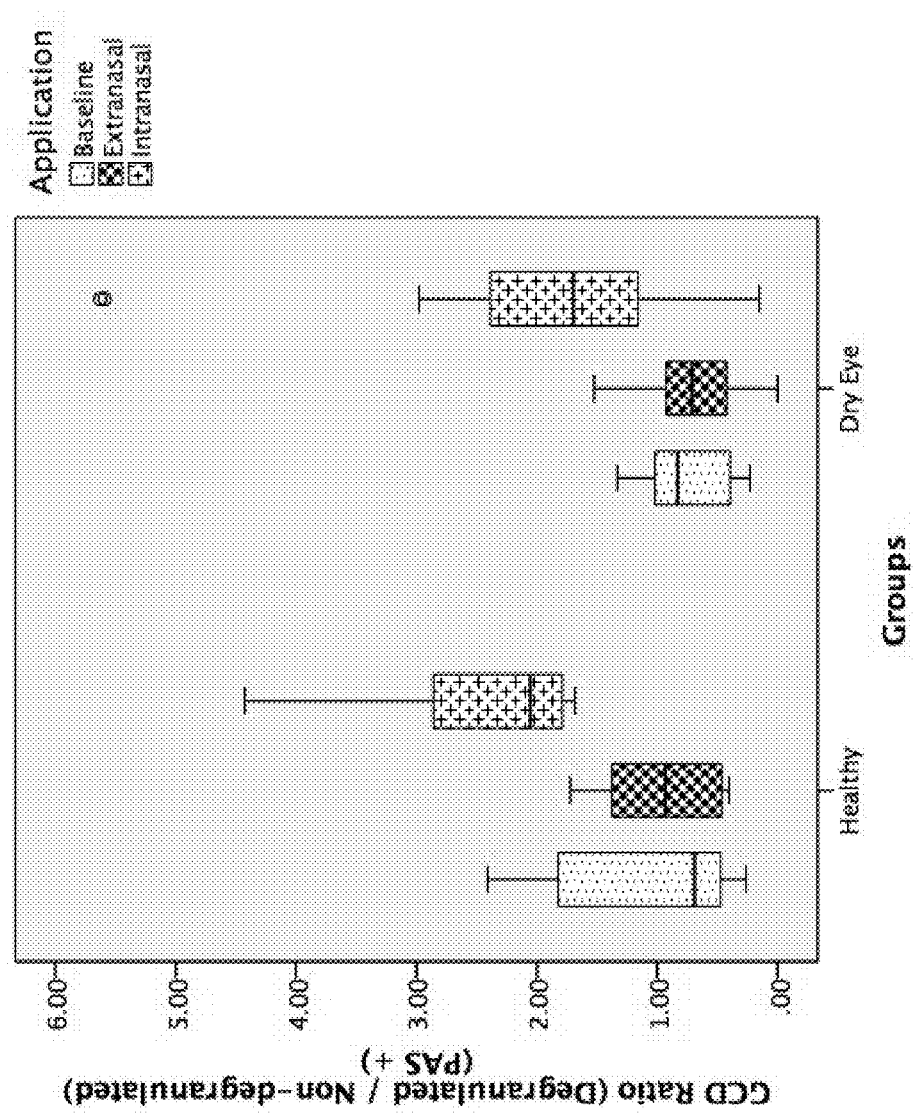
FIG. 17 is a graph of the data provided in Table 4 relating to goblet cell density (GCD) ratio (degranulated/non-degranulated) in the conjunctiva of dry eye and healthy subjects stained with PAS.

Results obtained from the PAS staining were also statistically significant. As provided in Table 4 and FIG. 17, intranasal stimulation when compared to both baseline and extranasal stimulation demonstrated a significant increase in the degranulated to non-degranulated goblet cell density ratio in the conjunctiva of subjects with dry eye and in normal/healthy subjects. Specifically, there was a significant increase in the ratio of degranulated to non-degranulated goblet cell densities after the delivery of intranasal stimulation in dry eye subjects (2.02±1.41) compared to those taken at baseline (0.73±0.36, p=0.001) and after sham (extranasal) stimulation (0.69±0.39, p=0.001).

TABLE 4

| Groups | A- Baseline | B- Extranasal Application | C- Intranasal Application | P Values A-B | A-C | B-C |
|---|---|---|---|---|---|---|
| Dry Eye | 0.73 ± 0.36 | 0.69 ± 0.39 | 2.02 ± 1.41 | 0.606 | 0.001 | 0.001 |
| Healthy Subjects | 1.06 ± 0.72 | 1.02 ± 0.76 | 2.38 ± 0.84 | 0.909 | 0.007 | 0.003 |

Figure 18:
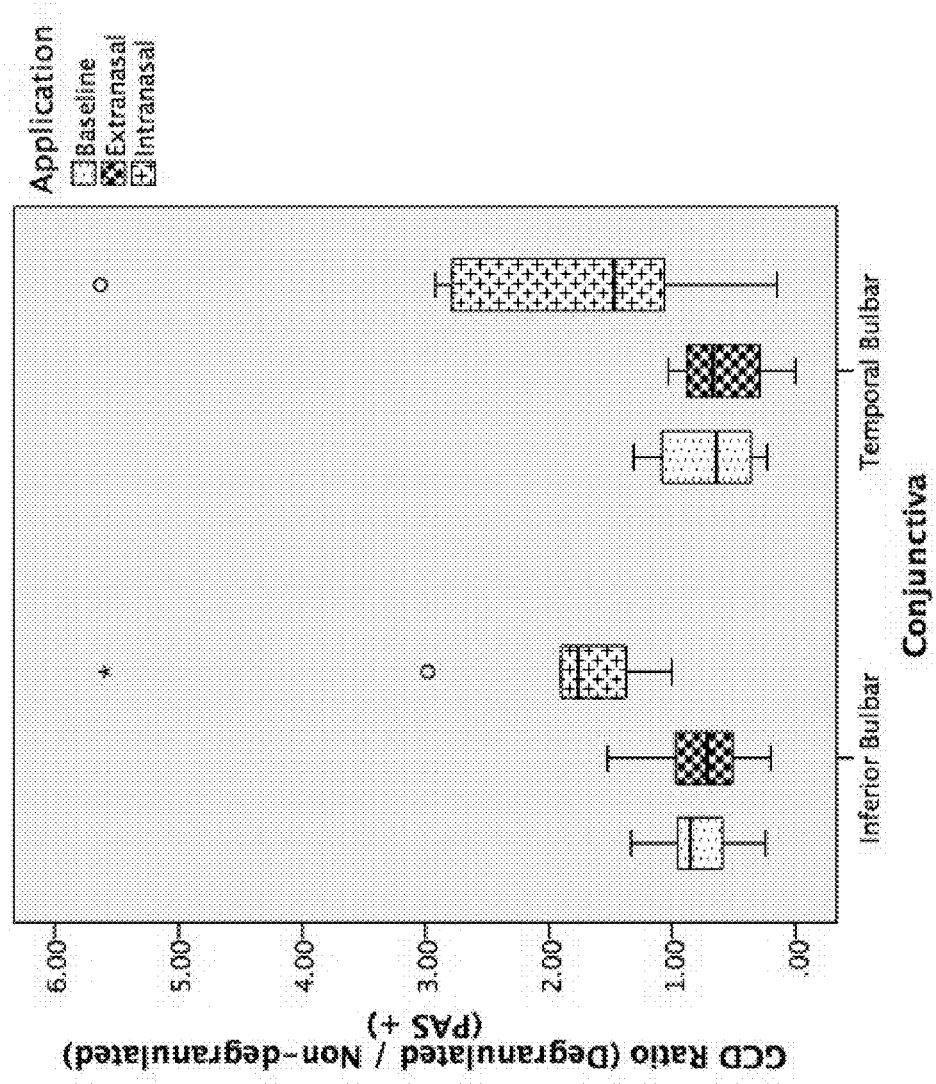
FIG. 18 is a graph of the data provided in Table 5 relating to goblet cell density (GCD) ratio (degranulated/non-degranulated) in the inferior and temporal bulbar conjunctiva of dry eye patients stained with PAS.

Data obtained from PAS staining also demonstrated that goblet cell degranulation occurred in various areas of the conjunctiva on the eye (bulbar conjunctiva). IC samples taken from the inferior bulbar conjunctiva (IB) and temporal bulbar conjunctiva (TB) of subjects with dry eye and normal/healthy subjects showed an increase in degranulated goblet cell densities, as provided below in Table 5, and graphically represented in FIG. 18.

TABLE 5

| Conjunctiva | A- Baseline | B- Extranasal Application | C- Intranasal Application | P Values A-B | A-C | B-C |
|---|---|---|---|---|---|---|
| Dry Eye - IB (n: 10) | 0.77 ± 0.34 | 0.79 ± 0.42 | 2.09 ± 1.34 | 0.802 | 0.026 | 0.029 |
| Dry Eye - TB (n: 10) | 0.70 + 0.40 | 0.58 + 0.36 | 1.95 + 1.55 | 0.432 | 0.014 | 0.01 |

IB: Inferior bulbar (Non-exposed zone),
TB: Temporal bulbar (Exposed zone)

Example 2: Tear Meniscus Height (TMH)

During the treatment visits outlined above, tear meniscus height was measured by AS-OCT (Anterior Optical Coherence Tomography) (RTVue; Optovue INC., Fremont, Calif.) before and after stimulation applications. The study eye was the eye with the lowest tear meniscus height prior to the first stimulation application, or, if both eyes were equal, the right eye was considered the study eye.

Figure 19:
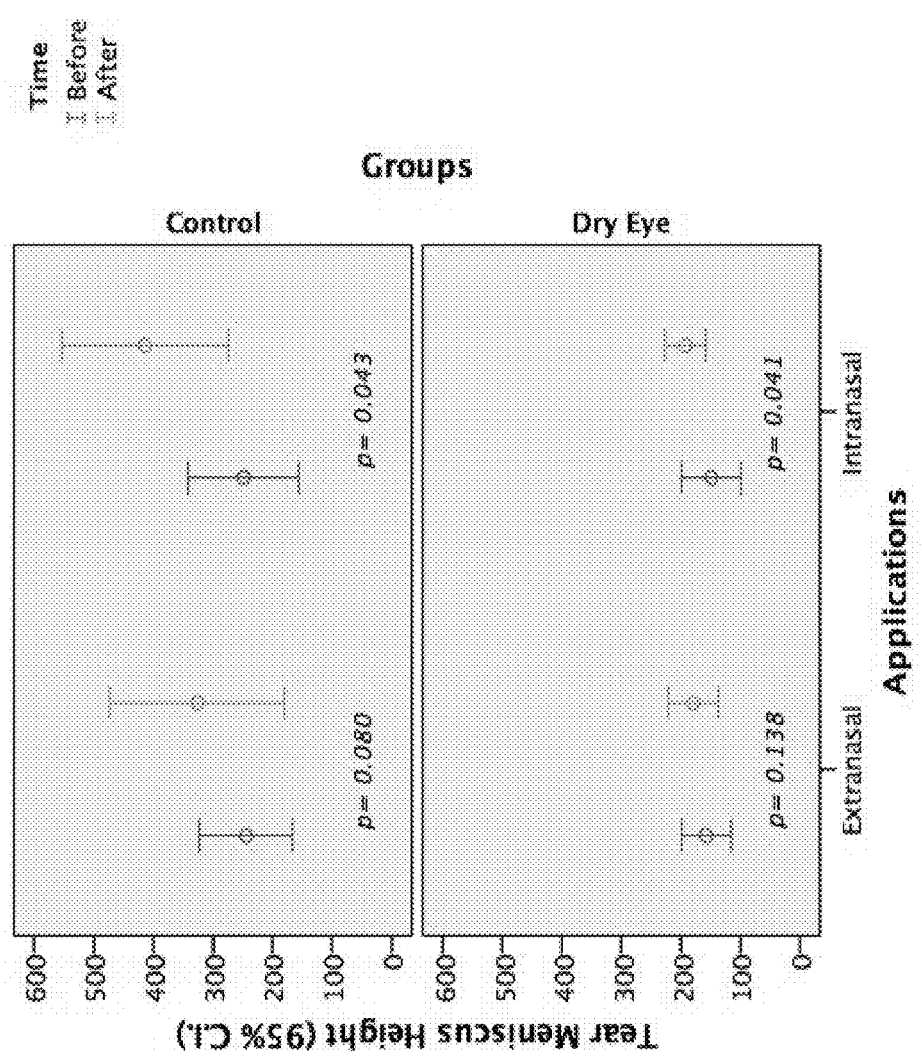
FIG. 19 present graphs of the data provided in Table 6 relating to tear meniscus height changes before and after extranasal and intranasal stimulation application in dry eye and control subjects.
Figure 20:
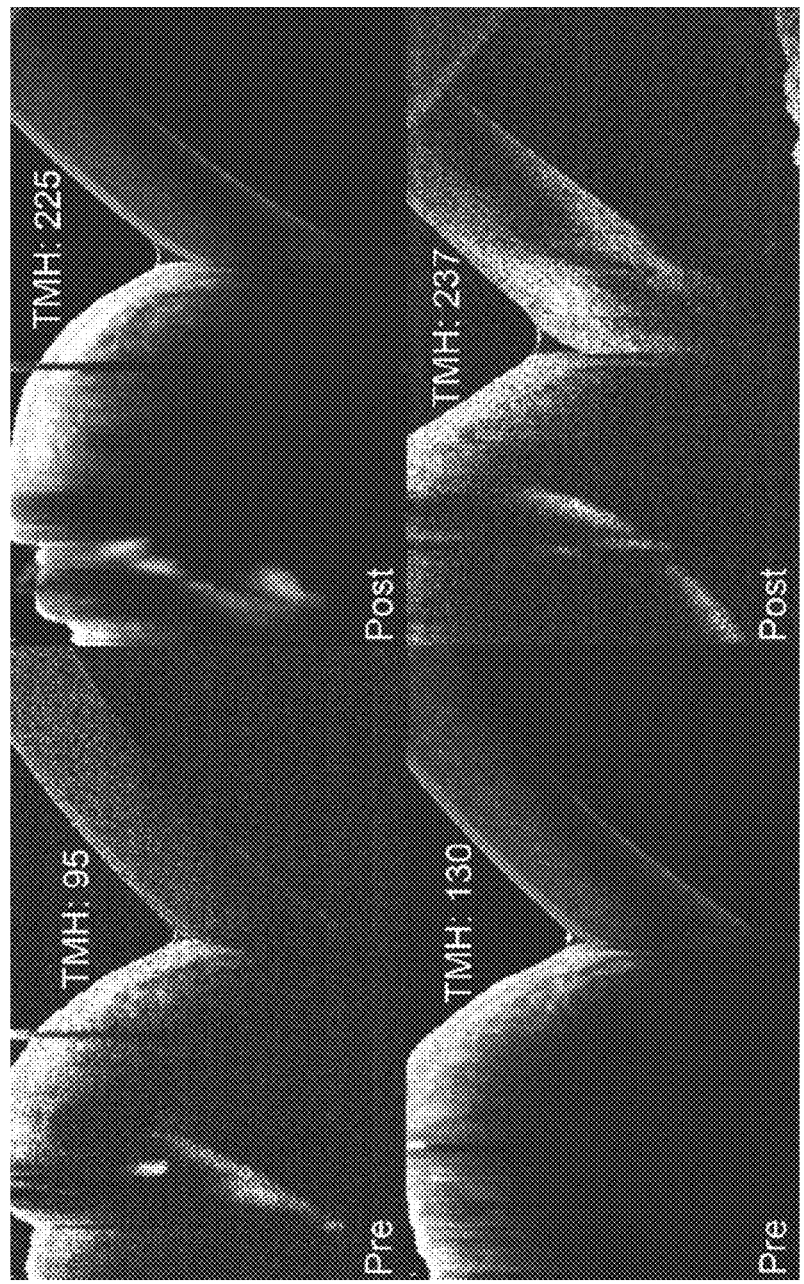
FIG. 20 presents optical coherence tomography images showing the change in height in the right eye (top) and left eye (bottom) before (left) and after (right) the intranasal application of stimulation in one dry eye subject with Sjögren's syndrome.

As shown by the data in Table 6, which is graphically represented in FIG. 19, tear meniscus height revealed a statistically significant increase after intranasal application in both dry eye and control groups (p value equal to about 0.04 for both). In one dry eye subject with Sjögren's syndrome, intranasal stimulation increased tear meniscus height in the right eye by about 135% (95 μm to 225 μm) and in the left eye by about 82% (130 μm to 237 μm), as illustrated in FIG. 20.

TABLE 6

| Groups | Application | Pre/Post | Mean ± SD | P Value |
|---|---|---|---|---|
| Dry Eye | Extranasal | Pre | 157.60 ± 57.59 | 0.138 |
|  |  | Post | 178.80 ± 58.57 |  |

TABLE 6-continued

| Groups | Application | Pre/Post | Mean ± SD | P Value |
|---|---|---|---|---|
|  | Intranasal | Pre | 149.50 ± 69.76 | 0.041 |
|  |  | Post | 192.60 + 47.34 |  |
|  | Extranasal | Pre | 244.80 ± 63.24 | 0.080 |

TABLE 6-continued

| Groups | Application | Pre/Post | Mean ± SD | P Value |
|---|---|---|---|---|
| Control |  | Post | 326.20 ± 118.27 |  |
|  | Intranasal | Pre | 249.00 ± 75.13 |  |
|  |  | Post | 414.00 ± 112.12 |  |

Example 3: Tear Fluid Composition

During the treatment visits outlined above, tear fluid was collected before and after each intranasal and extranasal stimulation. Tear samples were collected using a microcapillary tube from the tear lake near the temporal canthus without touching the globe. Tear collection continued until a maximum of 5 μL was collected from each eye, or until 5 minutes had elapsed.

The tear samples were analyzed for a variety of factors and inflammatory mediators. Although not statistically significant, there was a decrease in MMP-9 and IL-8 concentrations in the tear samples after the intranasal application of stimulation, which appeared to more be prominent in the dry eye group. MMP-9 concentration data from subjects who revealed a decrease compared to controls after intranasal stimulation application are provided in Table 7 and in FIG. 21. Data illustrating the decrease in IL-8 concentration as compared to controls after intranasal stimulation application is provided in FIG. 22. Additional studies will be conducted to obtain data from more subjects.

TABLE 7

| | Control (n: 5) | | | | Dry Eye (n: 10) | | | |
|---|---|---|---|---|---|---|---|---|
| | Extranasal (n: 2) | | Intranasal (n: 2) | | Extranasal (n: 3) | | Intranasal (n: 3) | |
| | Before | After | Before | After | Before | After | Before | After |
| MMP-9 (pg/ml) | 267.34 | 0.6 | 1336.28 | 37.5 | 1435.71 | 0.6 | 3372.37 | 0.6 |

Example 4: Goblet Cell Morphology

Data relating to morphological goblet cell (GC) changes before and after intranasal stimulation was obtained from a single center, single-arm, study that included 15 dry eye subjects (22 eyes). Intranasal stimulation was delivered using a handheld stimulation device as described in FIGS. 4A-4E.

Laser in vivo corneal confocal microscopy (laser IVCM) images were taken before and after approximately three minutes of intranasal stimulation application at the inferonasal area of the bulbar conjunctiva. GCs were analyzed and measured by ImageJ™ software. Three images from each subject were selected according to their quality and accuracy to be further analyzed by two masked observers. GCs were selected according to the following criteria: 50<area<150 μm$^2$, round or oval shaped, highlighted from the background, and well defined borders. All data are shown as mean±SD. Mean data were compared using a paired t-test. P values <0.05 were considered statistically significant.

Morphological analysis was performed for a total of 755 GCs pre- and 712 GCs post-application of the intranasal stimulation. Mean pre- and post-GC areas were 67.52±40.03 μm$^2$ and 58.72±31.16 μm$^2$, respectively. The mean change in area, 8.8±8.8 μm, representing a 13.03% reduction following use of the stimulation device, was statistically significant (p<0.001). Mean pre- and post-stimulation GC perimeters were 48.78±21.84 μm and 42.79±19.25 μm, respectively. The mean change in perimeter, 5.99±2.59 μm, representing a 12.27% reduction following use of the intranasal stimulator, was statistically significant (p<0.001).

Overall, a comparison of the laser IVCM images showed a significant reduction in GC area and perimeter within three minutes of stimulation, demonstrating a direct effect on GCs.

Example 5: Increased Secretion of Lysozyme and Lactoferrin

Increased aqueous tear production after intranasal stimulation was demonstrated in Example 2. In this Example, intranasal stimulation was also shown to promote release of other proteins from secretory granules in the lacrimal gland.

Fifty-five (55) dry eye subjects were enrolled in a single-arm study. Intranasal stimulation was delivered to the subjects using a handheld stimulation device as described in FIGS. 4A-4E for approximately 3 minutes. Tear samples (up to 10 μl) were collected using microcapillary tubes prior to and 5 minutes after use of the handheld stimulation device. Tear total protein concentration was determined using a micro-bicinchoninic acid protein assay and then the tear proteins separated by sodium dodecyl sulfate polyacrylamide gel electrophoresis (SDS-PAGE) followed by Western blotting.

Data from the single-arm study is provided below as mean±SD (standard deviation). Mean differences in concentration (post-stimulation minus pre-stimulation) were evaluated by determining an equivalence margin and comparing the 95% confidence interval (CI) of the mean difference to the margin.

Mean pre-stimulation and post-stimulation total protein concentrations were 12.6±5.0 μg/μl and 11.9±4.0 μg/μl, respectively. An equivalence margin of ±2.52 μg/μl (20% of the pre-stimulation mean) was used to evaluate the equivalence of pre-stimulation and post-stimulation total protein concentration. The 95% CI [−2.11, 0.58], of the mean difference in total protein concentration (−0.76±4.85 μg/μl), fell within the equivalence margin. An equivalence margins of 0.20 μg/μl (20% of the pre-stimulation relative means) was used to evaluate the equivalence of the relative amounts of pre-stimulation and post-stimulation lysozyme and lactoferrin concentration. The 95% CI [−0.02, 0.09], of the mean difference in relative lysozyme concentration (−0.04±0.19), and the 95% CI [0.005, 0.22], of the mean difference in relative lactoferrin concentration (0.11±0.37), both fell within the equivalence margins.

The invention claimed is:

1. A method for increasing ocular mucin on an ocular surface of a subject, comprising:
    applying one or more active agents to the ocular surface prior to intranasally delivering an electrical stimulation to the subject, thereby increasing a density of goblet cells on the ocular surface, the one or more active agents comprising cyclosporine;
    intranasally delivering the electrical stimulation to the subject after applying the one or more active agents to the ocular surface; and
    stimulating release of the ocular mucin from the goblet cells,
    wherein the increased density of goblet cells and the released ocular mucin from the goblet cells improves a condition of an eye of the subject.

2. The method of claim 1, wherein the electrical stimulation is intranasally delivered for at least three minutes.

3. The method of claim 2, further comprising:
    measuring an impedance or an electromyogram signal from a facial muscle of the subject; and
    verifying, based on the measured impedance or electromyogram signal, the intranasal delivery of the electrical stimulation for at least three minutes.

4. The method of claim 1, wherein the electrical stimulation is intranasally delivered for at least 30 seconds.

5. The method of claim 4, further comprising:
measuring an impedance or an electromyogram signal from a facial muscle of the subject; and
verifying, based on the measured impedance or electromyogram signal, the intranasal delivery of the electrical stimulation for at least 30 seconds.

6. The method of claim 1, further comprising repeating the intranasal delivery of the electrical stimulation.

7. The method of claim 1, wherein the electrical stimulation is intranasally delivered to a nasal mucosa.

8. The method of claim 1, wherein the condition of the eye is an ocular surface disease.

9. The method of claim 1, wherein the condition of the eye is dry eye.

10. The method of claim 1, wherein the condition of the eye is ocular inflammation.

11. The method of claim 10, wherein the ocular inflammation is due to Sjögren's syndrome.

12. The method of claim 1, further comprising administering an additional treatment for the condition of the eye.

13. The method of claim 12, wherein the additional treatment comprises application of artificial tears to the ocular surface.

14. The method of claim 12, wherein the additional treatment comprises application of one or more second active agents to the ocular surface.

15. The method of claim 14, wherein the one or more second active agents comprises lifitegrast.

16. The method of claim 14, wherein the one or more second active agents comprises one or more antibacterial agents, one or more anti-inflammatory agents, one or more antihistamines, one or more immunomodulators, one or more immunohistomodulators, or combinations thereof.

17. The method of claim 1, wherein the intranasal delivery of the electrical stimulation comprises delivering an electrical stimulus comprising a waveform having on and off periods.

18. The method of claim 1, wherein the electrical stimulation is intranasally delivered using a stimulator, the stimulator comprising a stimulator body and a stimulator probe, wherein the stimulator probe comprises a nasal insertion prong.

19. The method of claim 18, further comprising:
positioning a portion of the nasal insertion prong in contact with a nasal mucosa.

20. The method of claim 19, wherein the portion of the nasal insertion prong in contact with the nasal mucosa is in proximity to the anterior ethmoidal nerve.

21. The method of claim 18, wherein the nasal insertion prong comprises a hydrogel electrode.

22. The method of claim 18, wherein the stimulator body is sized for holding in one hand.

23. The method of claim 18, wherein the stimulator probe comprises two nasal insertion prongs.

24. The method of claim 23, wherein the two nasal insertion prongs are biased toward each other.

25. The method of claim 24, wherein the bias of the two nasal insertion prongs holds the stimulator in the nose during the intranasal delivery of the electrical stimulation.

26. The method of claim 1, wherein the intranasal delivery of the electrical stimulation acutely increases a concentration of the ocular mucin on the ocular surface.

27. The method of claim 1, wherein the intranasal delivery of the electrical stimulation results in a sustained increase in a concentration of the ocular mucin on the ocular surface.

28. The method of claim 1, wherein the released ocular mucin repairs at least a portion of an ocular glycocalyx.

29. The method of claim 1, further comprising identifying an optimal stimulation location for intranasally delivering the electrical stimulation.

30. The method of claim 29, wherein the identifying the optimal stimulation location comprises monitoring impedance or obtaining feedback from an electromyogram (EMG) signal from a facial muscle near the nose, cheeks, or around the eyes.

31. The method of claim 30, wherein the impedance or the EMG signal is measured intranasally by a device that delivers the electrical stimulation.

32. The method of claim 30, wherein the impedance or the EMG signal is measured using an extranasal device.

33. The method of claim 32, wherein the extranasal device comprises a nose strip.

34. The method of claim 1, further comprising optimizing one or more parameters of the intranasally delivered electrical stimulation, wherein the one or more optimized parameters is selected from the group consisting of duration of stimulation, type of stimulation waveform, frequency of the stimulation waveform, amplitude of the stimulation waveform, pulse width of the stimulation waveform, and combinations thereof.

35. The method of claim 34, wherein the one or more optimized parameters is duration of stimulation.

36. The method of claim 34, wherein the one or more optimized parameters is amplitude of the stimulation waveform.

* * * * *